United States Patent
Toth et al.

(10) Patent No.: US 6,480,141 B1
(45) Date of Patent: Nov. 12, 2002

(54) DETECTION OF CONTRABAND USING MICROWAVE RADIATION

(75) Inventors: Richard P. Toth, Albuquerque, NM (US); Guillermo M. Loubriel, Albuquerque, NM (US); Larry D. Bacon, Albuquerque, NM (US); Robert D. Watson, Tijeras, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/805,650

(22) Filed: Mar. 13, 2001

(51) Int. Cl.[7] .................. G01S 13/00; G01N 22/00
(52) U.S. Cl. .................. 342/22; 342/27; 324/639
(58) Field of Search ............... 342/22, 27; 324/637, 324/639

(56) References Cited

U.S. PATENT DOCUMENTS

| | | | |
|---|---|---|---|
| 3,562,642 A | 2/1971 | Hochschild | 324/58.5 |
| 4,607,212 A | 8/1986 | Jakkula | 324/58.5 |
| 4,975,968 A | 12/1990 | Yukl | 382/1 |
| 5,073,782 A | 12/1991 | Huguenin et al. | 342/179 |
| 5,177,444 A | 1/1993 | Cutmore | 324/637 |
| 5,177,445 A * | 1/1993 | Cross | 324/637 |
| 5,216,372 A | 6/1993 | Zoughi et al. | 324/644 |
| 5,455,590 A * | 10/1995 | Collins et al. | 342/179 |
| 6,057,761 A | 5/2000 | Yukl | 340/568.1 |

FOREIGN PATENT DOCUMENTS

GB      2199715      * 7/1988

OTHER PUBLICATIONS

Sheen et al., "Three–Dimensional Millimeter–Wave Imaging for Concealed Weapon Detection", IEEE Transactions on Microwave Theory and Techniques, vol. 49, No. 9, Nov. 2000.*
Bhardwaj, M. C., "Innovation in non–contact ultrasonic analysis: applications for hidden objects detection," Springer–Verlag, Oct. 24, 1997, pp. 188–196.
"Spatial Dynamics, Inc.", http://cgi.rmci.net/spatial/, Jan. 26, 2001.
"Waveguide Horns", Narda, an L3 Communications Company, pp. 394–398.
"STG 2815 Contraband and Bug Detector" Surveillance Technology Group.

* cited by examiner

Primary Examiner—Ian J. Lobo
(74) Attorney, Agent, or Firm—Robert D. Watson; Fred A. Lewis

(57) ABSTRACT

The present invention relates to a method and system for using microwave radiation to detect contraband hidden inside of a non-metallic container, such as a pneumatic vehicle tire. The method relies on the attenuation, retardation, time delay, or phase shift of microwave radiation as it passes through the container plus the contraband. The method is non-invasive, non-destructive, low power, and does not require physical contact with the container.

67 Claims, 19 Drawing Sheets

DETECTION OF CONTRABAND USING MICROWAVE RADIATION

FEDERALLY SPONSORED RESEARCH

The United States Government has rights in this invention pursuant to Department of Energy Contract No. DE-AC04-94AL85000 with Sandia Corporation.

FIELD OF THE INVENTION

The present invention relates generally to security surveillance systems using electromagnetic radiation, and more particularly to the use of microwave radiation to detect contraband hidden inside of a non-metallic container, such as a vehicle tire.

BACKGROUND OF THE INVENTION

Contraband, such as illegal drugs, explosives, weapons, and cash, is commonly hidden inside of containers to avoid detection when crossing the borders of a country or state. In the United States, a majority of illegal drugs and cash are carried across the border at official ports of entry by automobiles and trucks. Contraband can be hidden inside of false compartments inside of vehicles, such as within gas tanks, behind structural or cosmetic panels, and inside of pneumatic tires. The U.S. Customs Service is tasked with inspecting goods that travel across our borders.

Traditionally, X-rays have been used to provide a two-dimensional snapshot of objects hidden inside of an opaque container. However, X-rays are generally poor at imaging low-density materials, can pose a radiation hazard to the public and operating personnel, and generally require relatively large and expensive equipment. Ultrasonic methods have also been used, but these require the use of a coupling agent (e.g., gel) placed in-between the transducer and the container. Alternatively, thermal neutron analysis has been used, but the equipment is very expensive and large. Hand-held detectors (i.e., dosimeters) using gamma rays have been used, but these units have a limited depth of penetration and require using a hazardous radioactive source.

For detecting contraband hidden inside of pneumatic tires, additional techniques have been used, such as: drug-sniffing dogs; striking of the tire sidewalls with hammers or mallets while listening to the acoustic signature; and visual inspection of the tire for unusual signs of wear caused by unbalanced tires packed unevenly with contraband. Other visual clues may be used, such as viewing new or old tires mixed in with the vehicle's normal set; or dirt (or the lack of it) on selected tires. When these indicators show that there is something unusual about the vehicle or its tires while parked in the primary inspection area, the vehicle is then directed to the secondary stage of inspection, where a second, closer look is taken, tires removed, etc.

Microwave radiation (i.e., 0.5–40 GHz) has been used to detect contraband hidden underneath a person's clothes and inside of luggage or baggage. See, for example, U.S. Pat. No. 6,057,761 to Yukl; U.S. Pat. No. 5,073,782 to Huguenin, et al.; and U.S. Pat. No. 4,975,968 to Yukl. These systems measure the microwave signal reflected from a sample located inside of an interrogation volume. The unique characteristics of the reflected microwave signal can indicate contraband hidden within. Commonly, a single transceiver unit (i.e., combined transmitter and receiver), is used for operating in the reflection mode. However, a large signal reflected from a thick-walled container, such as the sidewall of a rubber tire, may not carry sufficient information (or have enough sensitivity) to detect a low-density object hidden inside (such as a 5-lb bag of cocaine). Regardless of whether the tire is empty or contains a bag of contraband, the reflected microwave signal is essentially unchanged, which limits its usefulness as a detector.

Microwave radiation has also been used in the transmission mode for characterizing non-metallic objects. By transmission mode, we mean that some of the microwave signal passes completely through the container, which attenuates and slows down (i.e., retards) the microwave. The phase of the microwave can also change when passing through the container. The microwave that passes through the container (i.e., the transmitted microwave) is typically detected by a separate receiver located on the opposite side of the container from the microwave transmitter.

In U.S. Pat. No. 4,607,212 Jakkula describes a method of transmitting pure TEM wave mode microwave radiation through a piece of lumber, and then monitoring the generation of a TM wave mode component in the transmitted wave created by the presence of a knot in the lumber. However, Jakkula does not describe a system for detecting contraband hidden inside of a container.

In U.S. Pat. No. 5,177,444 Cutmore describes a method of measuring the unburnt carbon content of fly ash, comprising passing a microwave through a sample of fly ash and then measuring the attenuation and phase shift of the signal passed through the sample (with respect to the launched signal) to produce a measure of the unburnt carbon content. However, Cutmore does not describe a system for detecting contraband hidden inside of a container.

The measurement of microwave radiation transmitted through an object has also been used to measure the moisture content of wood and paper; to detect the location and depth of steel belts in tire treads; and to monitor the curing rate of rubber used in tire molds, two-part epoxy mixtures, and other polymeric reactions.

The need remains, therefore, for a safe, low power, low-cost, non-destructive contraband-detection method and apparatus that is capable of continuous operation at an official port of entry, year-round, with minimal attention by inspection personnel.

Against this background, the present invention was developed.

BRIEF DESCRIPTION OF THE DRAWINGS

The accompanying drawings, which are incorporate in and form part of the specification, illustrate various examples of the present invention and, together with the description, serve to explain the principles of the invention.

SUMMARY OF THE INVENTION

Figure 1A:
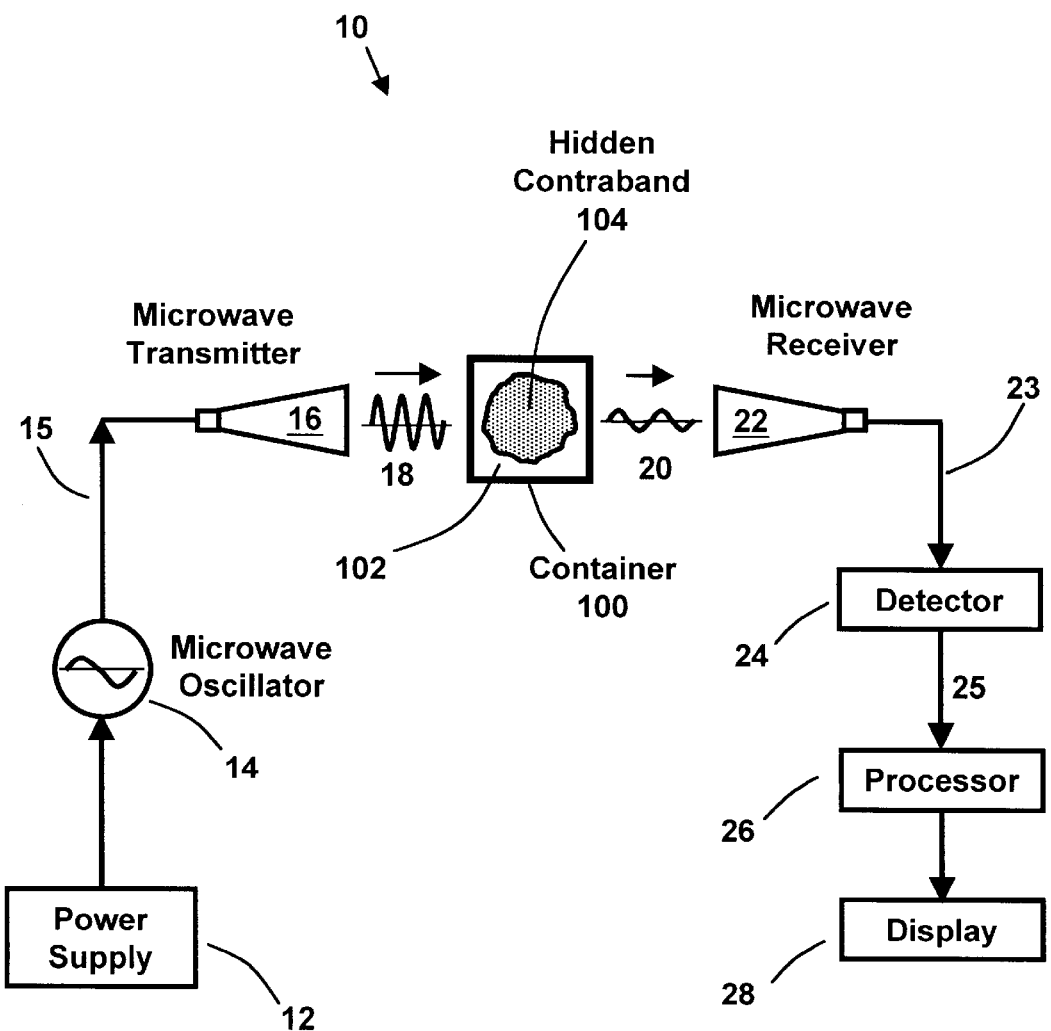
FIG. 1A illustrates a schematic layout of a first example of a system for detecting contraband hidden inside of a container, according to the present invention.

The present invention relates to a method and system for using microwave radiation to detect contraband hidden inside of a non-metallic container, such as a pneumatic vehicle tire. The method relies on the attenuation, retardation, time delay, phase shift, or disappearance of microwave radiation as it passes through the container plus the contraband. The method is non-invasive, non-destructive, low power, and does not require physical contact with the container. When used at official ports of entry to inspect vehicle tires, detection at this stage (i.e., the primary stage) virtually ensures a positive discovery during the subsequent secondary inspection stage. Successful operation of the present invention does not depend on the physical condition of the tire, the vehicle, driver, or passengers. Positive detection of contraband (or other abnormal contents of a container) is indicated by a significant change in the amplitude, speed, timing, or phase of a transmitted test microwave signal that has passed through the container (including disappearance of the signal). A receiver located on the opposite side of the container can receive the test microwave signal. Any significant change in a characteristic property of the test microwave signal (caused by interactions with the contraband hidden inside) is compared to a baseline value of the same characteristic property determined by measuring and analyzing microwave radiation transmitted through a similar container that has normal contents inside (e.g., does not have any contraband hidden inside).

The container, in general, may or may not be empty; however, the container should be non-metallic so that microwave radiation (i.e., the test microwave signal) can penetrate its walls. In the example of a tire (e.g., automobile, motorcycle, bicycle, or truck tires), the tire is normally "empty" and filled only with pressurized air. The presence of steel reinforcing belts in the tread region of the tire does not affect the present technique, because the microwaves can be transmitted through the sidewall of the tire (i.e., not through the tread region containing steel belts).

Contraband can be hidden inside of a metal box that is itself hidden inside of the tire. The metal box completely reflects and blocks the incident test microwave signal, thereby preventing any test signal from passing through the tire to the other side. In this situation, the received test signal would be essentially zero because no signal actually penetrates through the tire to reach the receiver. Comparison of the received signal (essentially zero amplitude, in this case) with the baseline signal measured on a normal, empty tire (large amplitude signal) reveals a large discrepancy or difference between the two signals. The results of this comparison therefore indicates the presence of abnormal contents within the tire. The method doesn't identify what the abnormal contents actually are inside the tire because the box is opaque to microwave radiation, only that something is suspicious, irregular or atypical about that specific tire. Subsequently, the tire can be subjected to other methods of inspection, or physically removed and inspected by hand, e.g., at a secondary inspection station, to positively identify the source of the anomalous readings.

Some examples of "normally-empty" containers include rolls of sheet goods having a hollow core (e.g., carpet rolls, paper rolls, textile rolls, plastic film rolls, toilet paper rolls). Other examples of "normally-empty" containers include: hollow piping, tubing, cement building blocks, wall cavities, unfilled glass or plastic bottles, and empty fiberglass shipping containers.

The non-metallic container can also be "normally-filled" with material or goods. For example, normally-filled containers can include: bundles of stacked lumber, bags of air mail, boxes of toilet paper rolls, boxes of paper goods, plastic bottles of powdered soap, bags of grass seed, etc. Illegal contraband can be placed inside the normally filled container, displacing some of the normal contents. The subsequent transmission of test microwaves through the container will be disturbed by the contraband if the dielectric constant (and other electrical properties, such as the loss tangent or dissipation factor, the dimensions of the material and/or flaws in the material, and the distance between the test part and the sensing element) of the hidden contraband is sufficiently different than the average or aggregate properties of the normally expected objects. This disturbance in the transmitted signal can indicate the presence of hidden contraband. If the disturbance or perturbation exceeds a pre-set threshold valve, the system can generate an alarm or alert signal indicating the possible presence of hidden contraband. In this case, the perturbation can manifest itself as either an increase or a decrease in the signal, depending on what normal contents have been displaced by the abnormal contents (e.g., contraband).

The method and apparatus of the present invention can be realized in two different systems based on a frequency-domain method or a time-domain method. In a frequency-domain system, the amplitude of the microwave radiation decreases (i.e., attenuates) as it passes through the container plus contraband, due to absorbtion, reflection, and scattering processes. For example, microwave radiation traversing an empty tire is attenuated less than a tire containing contraband. Alternatively, in a time-domain system, the speed or velocity of a pulse of microwave energy decreases as it passes through the container plus contraband. The reduction in the pulse's velocity can be translated into a measurable difference in the time period for the pulse to traverse across the container from one side to the other, i.e., the time-of-flight (TOF). For example, a pulse of microwave radiation traverses across an empty tire faster than a tire containing contraband. The time delay, of difference between the TOF for an empty tire, compared to the TOF for a filled tire, can indicate the presence of contraband. The pulse can also reflect multiple times off of internal surfaces within the container prior to eventually exiting the container's wall(s). Alternatively, unique information can be obtained by analyzing changes in the relative phase of the microwave signal as it passes through the container plus contraband. A combination of both frequency-domain and time-domain systems can be used, as well.

DETAILED DESCRIPTION OF THE INVENTION

FIG. 1A illustrates a schematic layout of a first example of a system for detecting contraband hidden inside of a non-metallic container, according to the present invention. Detection system 10 comprises a power supply 12 that provides electrical power to a microwave oscillator 14. Power supply 12 can be a low-power supply (e.g., less than 1 watt). Oscillator 14 generates microwave radiation, which we consider to cover the frequency range of approximately 0.5–40 GHz. Transmission line 15 carries microwave energy from oscillator 14 to transmitter 16. Transmitter 16 launches test microwave radiation 18 towards container 100. Cavity 102 inside of container 100 can be normally empty or normally filled with its typical, normal contents. Container 100 may (or may not) have contraband 104 hidden inside. After passing through container 100 (and, possibly, passing through hidden contraband 104), transmitted test microwave radiation 20 is received by microwave receiver 22. Receiver 22 transmits the received test signal 20 via transmission line 23 to detector 24. Detector 24 can convert the transmitted microwave signal 20 into a voltage signal 25 suitable for analysis by computer processor 26. Microwave detector 24 can be, for example; a crystal detector or diode device that rectifies the received microwave signal 20 to yield a voltage (e.g., millivolt level) that is proportional to the input level (i.e., square law detectors). Alternatively, detector 24 can be a thermally based sensor, such as a pyrometer or a bolometer. Generally, diode-based detectors respond faster than thermally based sensors, however, either type can be used for the present invention. Processor 26 compares one or more characteristic properties of voltage signal 25 with the same characteristic property of a baseline received signal (representative of a container with normal contents, e.g., without contraband) stored in a library or memory, and determines if container 100 contains any contraband or abnormal contents. A characteristic property can be the amplitude, velocity, time delay, phase, or disappearance of the test signal. Disappearance of the test microwave signal is equivalent to the signal having an amplitude that is below the detection threshold of the system (i.e., essentially zero amplitude). Voltage signal 25 can be displayed on display 28, which can be programmed to provide an alarm or provide other alerting functions if processor 26 detects the presence of contraband 104.

Variable levels of thresholds for alarming or alerting can be programmed, depending on the need to maximize the sensitivity of the system, without increasing the false alarm rate. Processor 26 can also perform the functions of data logging, record keeping, and surveillance. Processor 26 can include a neural net processor, which could be used to determine which frequencies provide the optimum contrast and maximum sensitivity for a given class of containers (e.g., semi-tractor trailer tires). Processor 26 and detector 24 can be combined into a single piece of equipment, such as a Wiltron Model 560A Scaler Network Analyzer. Detection system 10 can be operated in the frequency-domain system, the time-domain system, or a combination of both. Oscillator 14 can generate microwave radiation continuously (i.e., CW), in single-shot mode, or in repeated pulses (i.e., pulsed operation).

Oscillator 14 can be an yttrium-iron-garnet (YIG) oscillator tunable over a useful range of frequencies, for example, 2–4 GHz. Alternatively, oscillator 14 can be a Gunn diode oscillator (e.g., for X-band applications in the range of 8–12 GHz), or a voltage controlled oscillator (e.g., for C-band applications in the range of 4–6 GHz). Oscillator 14 can generate microwave radiation at a fixed frequency (e.g., 10 GHz), or at a variable frequency that is repeatedly swept from a minimum value (e.g., 4 GHz) to a maximum value (e.g., 6 GHz). Transmission lines 15 and 23 can be a waveguide, coaxial cable, strip line, or any other well-known microwave transmitting element. Transmitter 16 and receiver 22 face each other from opposite sides of container 100, and are aligned coaxially with each other to maximize reception efficiency. The actual distance between transmitter 16 and container 100, as well as the distance between receiver 22 and container 22, are not critical because of the very small loss of signal as microwaves 18 and 20 propagate through the short distance of air surrounding container 100. However, transmitter 16 and receiver 22 generally should be placed reasonably close to container 100 to minimize the overall size of detection system 10, and to minimize unnecessary spillover of microwave radiation beyond the sides of container 100.

Microwave transmitter 16 and microwave receiver 22 can comprise sensing or radiating elements, such as a microwave horn, dipole, dielectric rod antenna, slot radiator, iris radiator, microwave lens, or other elements well known in the art. Preferably, transmitter 16 and receiver 22 comprise a standard gain waveguide horn (rectangular opening with 16.5 dB gain), which is optimized for a particular range (i.e., bands) of frequencies. Standard horns are available from Narda Microwave Inc., and Waveline, Inc. that cover a variety of popular bands, including the C-band (3.95–5.85 GHz), XN-band (5.4–8.2 GHz), XB-band (7.05–10 GHz), and X-band (8.2–12.4 GHz). Special ISM (Instrument, Scientific, and Medical) fixed frequencies can also be used, because they don't require special approval of an operating license. Of particular interest is the ISM frequency of 5.8 GHz. Generally, the size of these standard gain horns decreases as the operating frequency increases. Higher frequencies are generally more desirable for the present invention because the transmitter/receiver antenna/horns are physically smaller, afford higher directionality and higher spatial resolution of the microwave beam, and can allow the use of commercially available off-the-shelf components, such as those used in radar speed guns (X-band at 10 GHz). The benefits of increasing the frequency must be balanced, however, with the need to penetrate a sufficient amount of microwave energy through the container plus contraband.

Figure 1B:
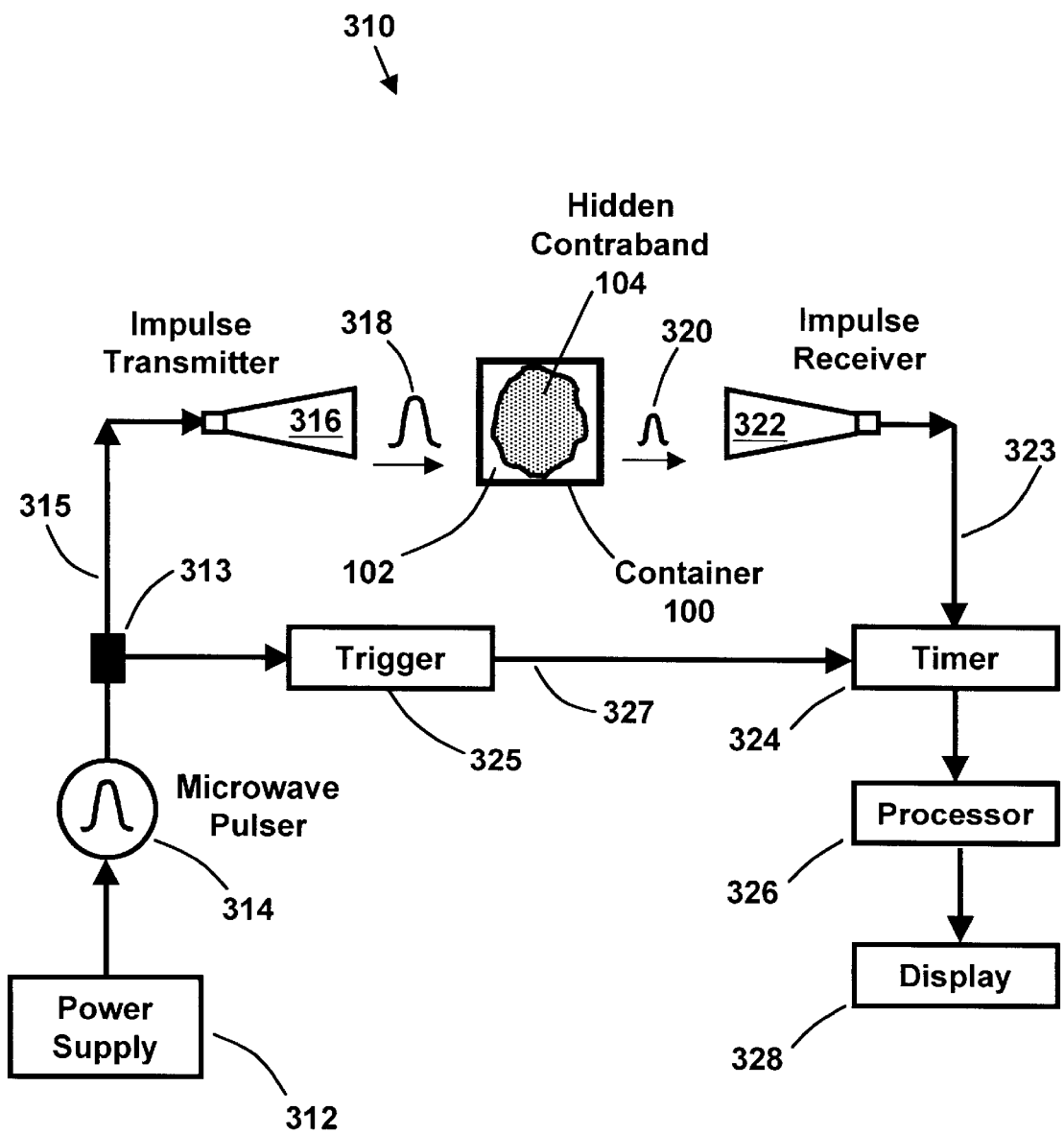
FIG. 1B illustrates a schematic layout of a second example of a system for detecting contraband hidden inside of a container, according to the present invention.

FIG. 1B illustrates a schematic layout of a second example of a system for detecting contraband hidden inside of a non-metallic container, according to the present invention. Detection system 310 comprises a power supply 312 that provides electrical power to a microwave pulser 314. Power supply 312 can be a low-power supply (e.g., less than 1 watt). Pulser 314 generates an ultra-short pulse whose pulse width (i.e., duration) is between 5 ps and 100 ns. Transmission line 315 carries most of the microwave energy from pulser 314 to impulse transmitter 316. A small amount of the energy from pulser 314 is diverted by pickoff 313 and trigger module 325, which delivers a timing signal (i.e., trigger signal 327) to timer 324. Impulse transmitter 316 launches microwave pulse 318 towards container 100. Cavity 102 inside of container 100 can be normally empty or normally filled with material. Container 100 may (or may not) have contraband 104 hidden inside. After passing through container 100 (and, possibly, passing through hidden contraband 104), transmitted microwave pulse 320 is received by impulse receiver 322. Receiver 322 transmits the received signal 320 via transmission line 323 to timer 324. Timer 324 detects the time at which pulse 320 is received by receiver 322, relative to the time when pulse 318 was launched, via trigger signal 327. Processor 326 compares one or more characteristic properties of the microwave pulse 320 with the same characteristic properties of a baseline signal (representative of a container without contraband or with normal contents) stored in a library or memory, and determines if container 100 contains any contraband or abnormal contents. The characteristic property can include the amplitude, velocity, time delay, and/or phase of the signal. The results of an analysis by processor 326 can be displayed on display 328, which can be programmed to provide an alarm or provide other alerting functions if processor 326 detects the presence of contraband 104.

Figure 2:
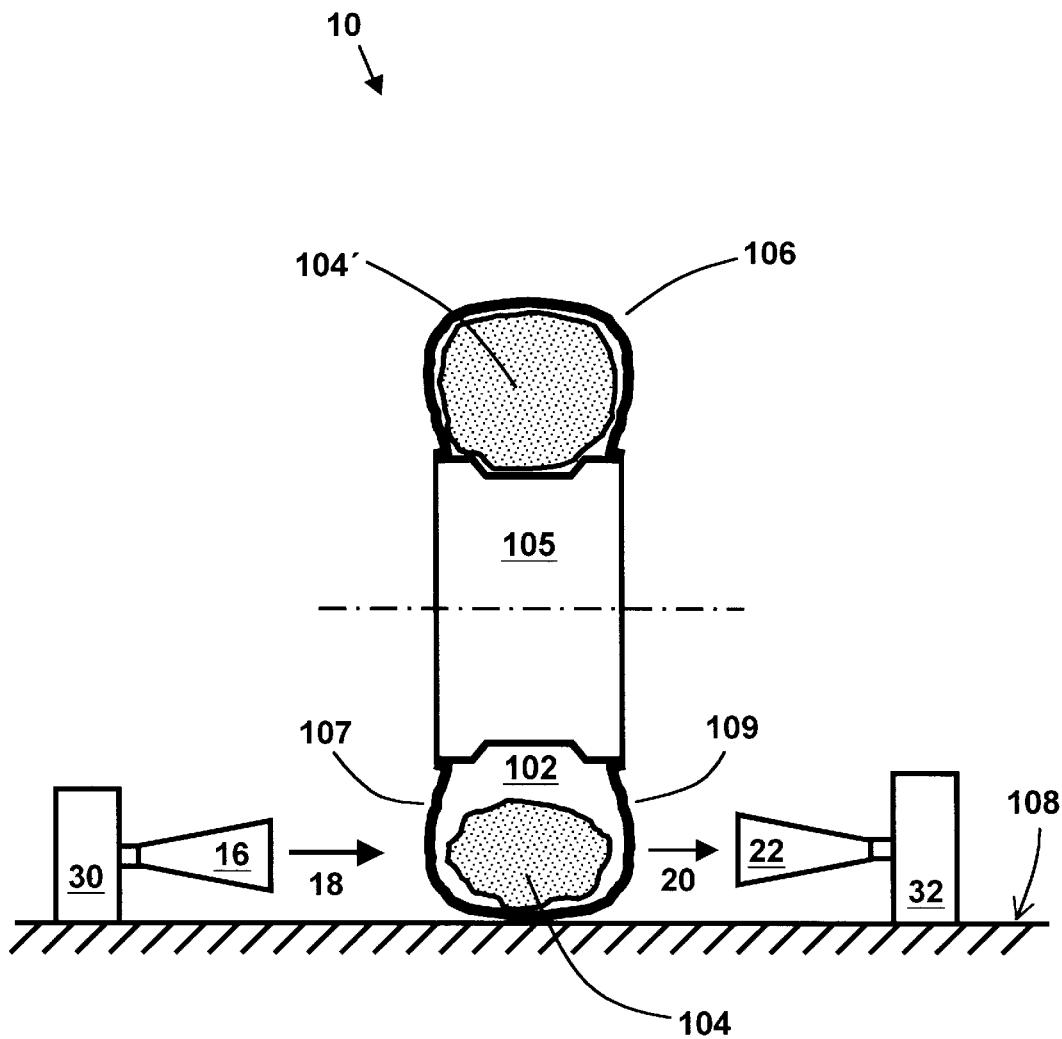
FIG. 2 illustrates a schematic side view of a third example of a system for detecting contraband hidden inside of a tire, according to the present invention.

FIG. 2 illustrates a schematic side view of a third example of a system for detecting contraband hidden inside of a tire, according to the present invention. Detection system 10 comprises a microwave transmitter 16 attached to a first support base 30 and a microwave receiver 22 attached to a second support base 32. Transmitter 16 is located diametrically opposed to receiver 22 (i.e., facing each other), with tire 106 disposed in-between (i.e., flanking the tire). Transmitter 16 and receiver 22 are coaxially aligned to maximize the reception of microwave signal 20, after the launched microwave signal 18 passes through the two sidewalls 107, 109 of tire 106 (plus contraband 104, if present). Tire 106 has a normally empty cavity 102 (i.e., air), and is mounted on wheel 105. Contraband 104 is shown as only partially filling cavity 102. However, contraband 104' is shown as significantly filling up cavity 102. It is most likely that illegal contraband would fill up as much of the empty space inside of a vehicle tire as possible (as illustrated by contraband 104').

Tire 106, while not part of the present invention, can be any type of normally-empty tire, including pneumatic tires, automobile, truck, semi-tractor trailer double-axle pair of tires, motorcycle tires, bicycle tires, and rigid-walled tires (unpressurized). The other components for system 10 (i.e., power supply, oscillator, detector, processor, and display, etc.) are not shown in FIG. 2 for sake of clarity. Support bases 30, 32 can be rigidly mounted on the ground 108, for example, at a US Customs port of entry primary inspection station, at a truck inspection station, or police station, etc. System 10 can also be temporarily set up at a temporary road block or checkpoint. Because the present invention uses a simple method and setup, it can be applied to all vehicles at a crossing point, removing any suggestion of bias on the part of the inspectors. The method is non-invasive, and eliminates the legal questions that can arise when standard contacting, hands-on methods are used for detection.

Figure 3:
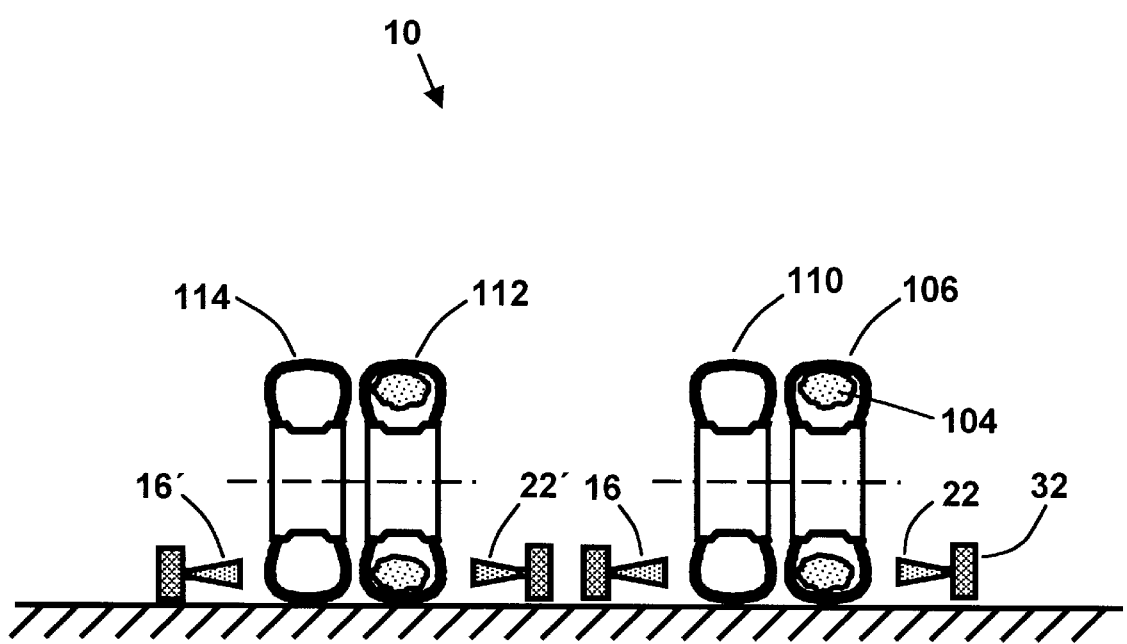
FIG. 3 illustrates a schematic side view of a fourth example of a system for detecting contraband hidden inside of a tire, according to the present invention.

FIG. 3 illustrates a schematic side view of a fourth example of a system for detecting contraband hidden inside of a tire, according to the present invention. In this example, system 10 is configured to inspect a pair of tires 106 and 110 mounted side-by-side on a single axle (i.e., double-axle style). Transmitter 16 is located on the left side of tire 110, while receiver 22 is located on the right side of the adjacent tire 106. With this arrangement, it will not be possible to determine which specific tire (of the pair of tires) actually has the hidden contraband; only that at least one of them has contraband 104 hidden inside. FIG. 3 also illustrates a duplicate pair of transmitter/receiver units 16', 22' disposed generally in-line with the axis of units 16, 22, which are arranged to detect contraband hidden inside of the adjacent pair of tires 112 and 114.

Figure 4A:
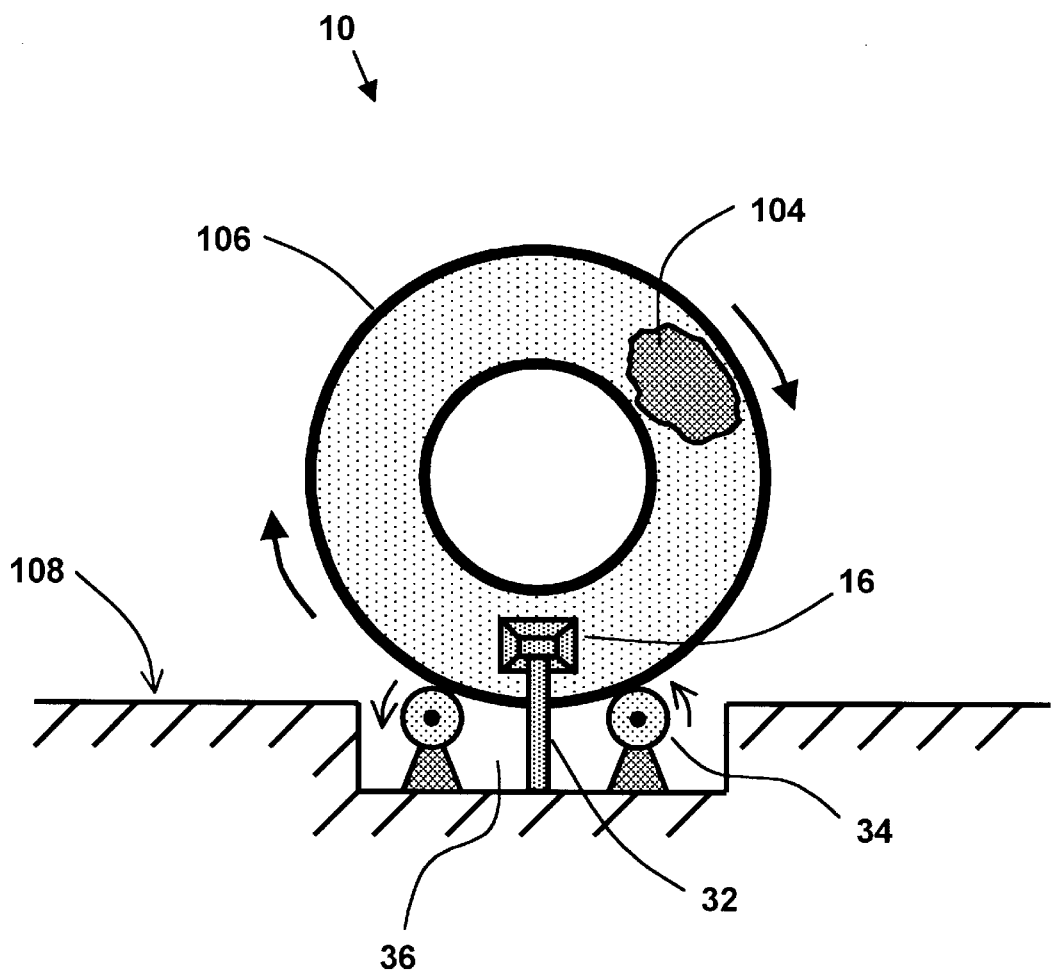
FIG. 4A illustrates a schematic side view of a fifth example of a system for detecting contraband hidden inside of a tire, according to the present invention.

FIG. 4A illustrates a schematic side view of a fifth example of a system for detecting contraband hidden inside of a tire, according to the present invention. In this example, tire 106 rests on a pair of rollers 34, which allow tire 106 to rotate while the vehicle remains stationary with respect to the ground 108. Rollers 34 can be mounted inside a cavity or well 36 recessed below the ground. Similar to vehicle emissions testing stations, this arrangement allows a single transmitter/receiver pair 16, 22 to irradiate and inspect the entire circumference of tire 106 as the tire rotates. Tire 106 can rotate one or more revolutions during inspection. By rotating tire 106 past a fixed transmitter/receiver unit, a single (isolated) bag of contraband 104 can be detected. A primary inspection station could have four such recessed wells 36, one for each tire on an automobile; or even more wells 36 for inspecting a semi-tractor trailer rig. Rollers 34 can be rotated by a motor (not shown), useful for inspecting tires that are freely-rotating (i.e., unpowered, free-wheeling).

Figure 4B:
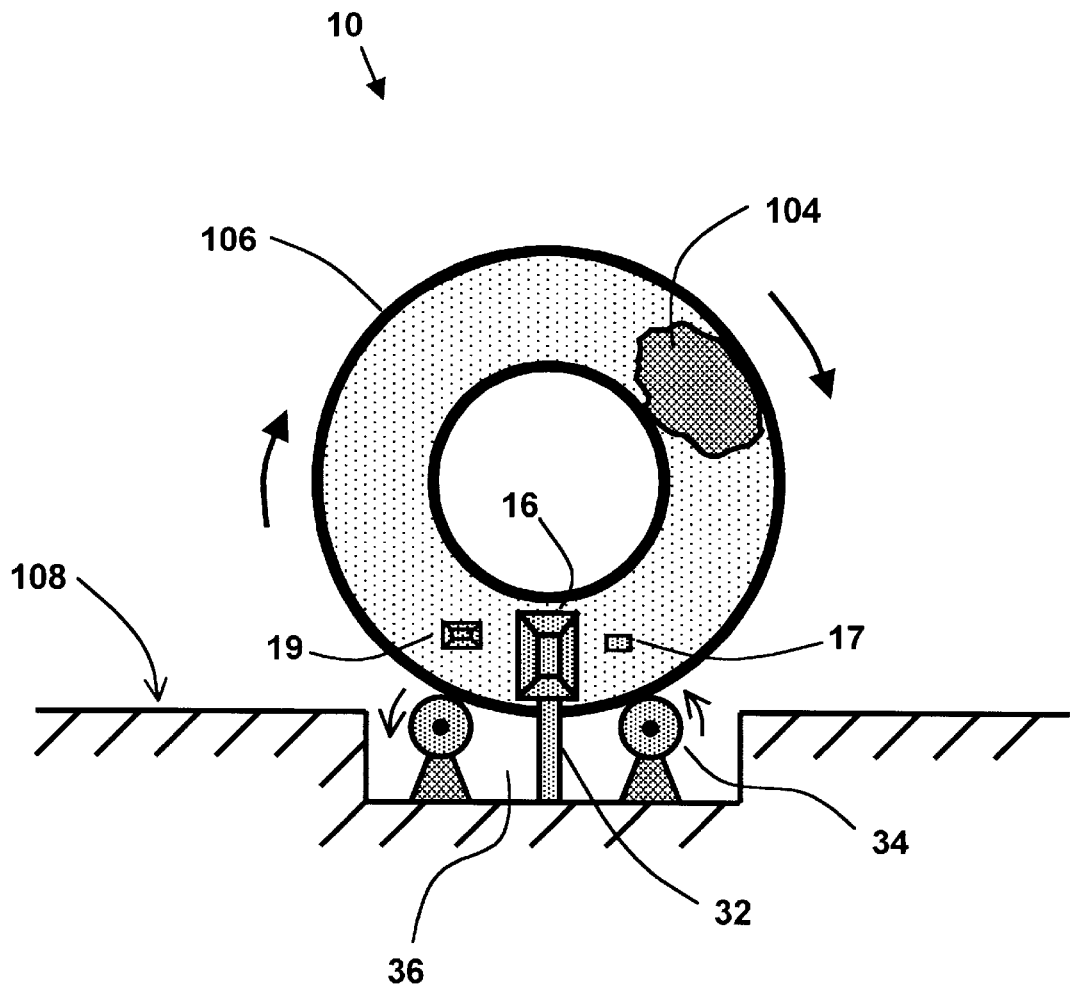
FIG. 4B illustrates a schematic side view of a sixth example of a system for detecting contraband hidden inside of a tire, according to the present invention.

FIG. 4B illustrates a schematic side view of a sixth example of a system for detecting contraband hidden inside of a tire, according to the present invention. Similar to the example shown in FIG. 4A, this version illustrates three different sized transmitter horns 16, 17, & 19 (along with their corresponding matched pairs of receivers, not shown, mounted adjacent to each other). The use of multiple transmitting horns 16, 17, 19 permits a larger total range of microwave frequencies to be used simultaneously (i.e., multiplexed). Multiple horns are useful because each standard horn typically only covers a subset of the entire microwave range from 0.5–40 GHz. For example, horn 16 could be a Narda model #643 covering 3.95 to 5.85 GHz; horn 17 could be a Narda model #642 covering 5.4 to 8.2 GHz; and horn 19 could be a Narda model #640 covering 8.2 to 12.4 GHz, thereby effectively covering the combined range from 3.5 GHz to 12.4 GHz. Increasing the total range of frequencies can provide improved capability to detect hidden contraband (including multiple types of contraband hidden within a single tire).

Figure 5:
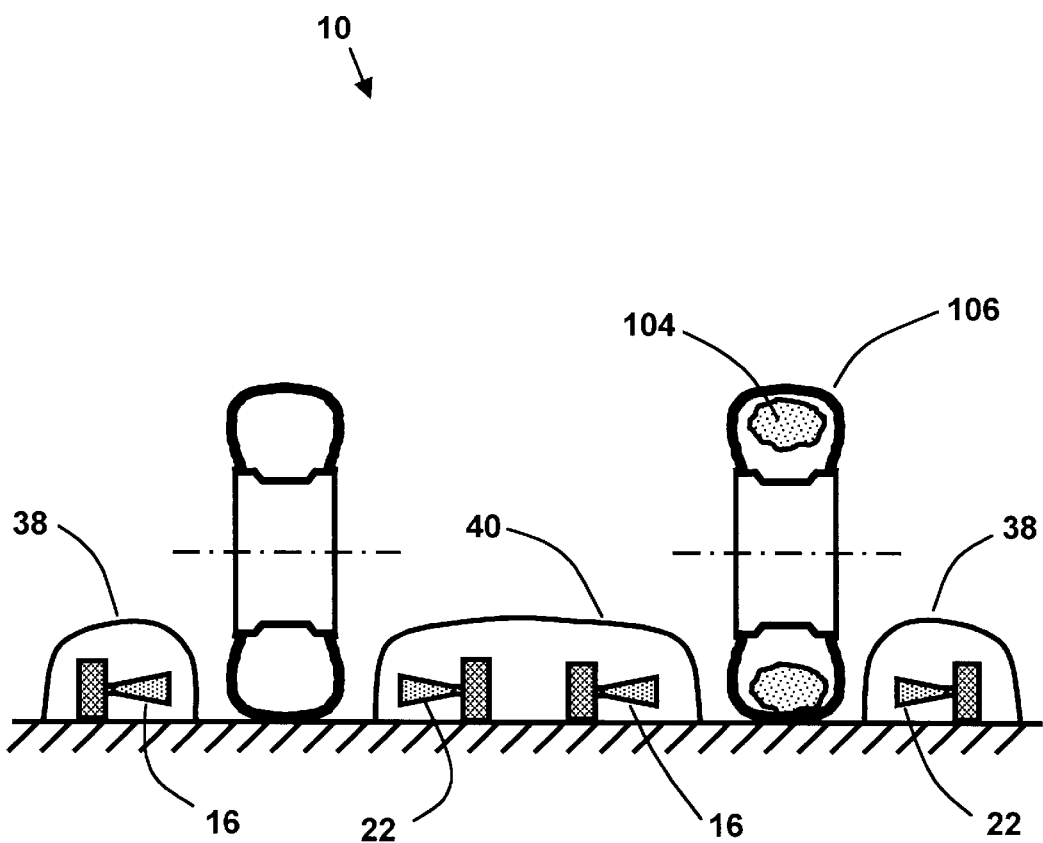
FIG. 5 illustrates a schematic side view of a seventh example of a system for detecting contraband hidden inside of a tire, according to the present invention.

FIG. 5 illustrates a schematic side view of a seventh example of a system for detecting contraband hidden inside of a tire, according to the present invention. In this example, microwave-transparent radome covers 38 and 40 surround and protect receiver 22, or pairs of receivers 22 and transmitters 16, respectively, from rain, snow, wind, mud, insects, etc. Radomes 38, 40 can be resin/fiberglass shells, or other microwave-transparent materials, well known in the art.

Figure 6:
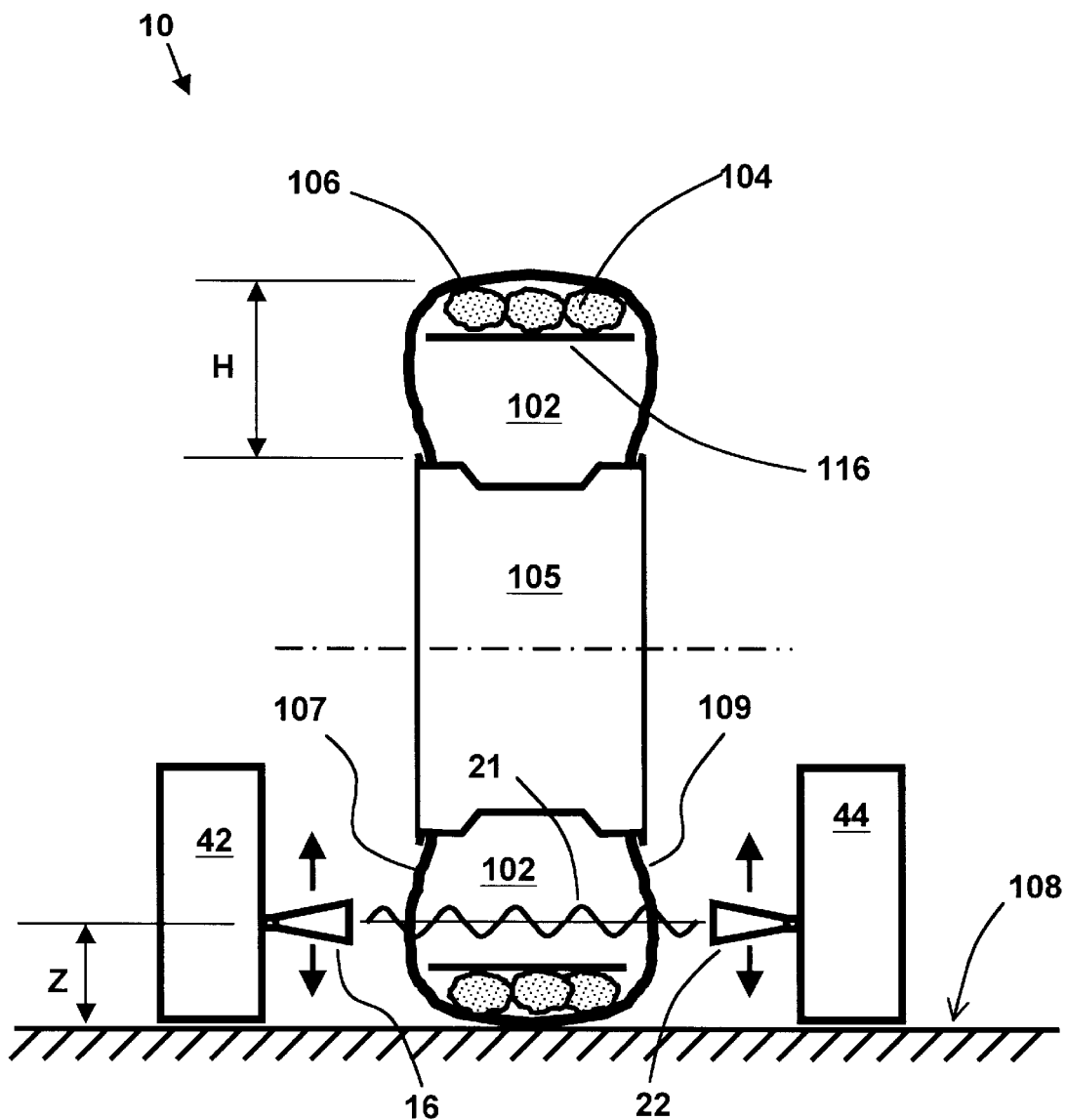
FIG. 6 illustrates a schematic side view of a eighth example of a system for detecting contraband hidden inside of a tire, according to the present invention.

FIG. 6 illustrates a schematic side view of a eighth example of a system for detecting contraband hidden inside of a tire, according to the present invention. In this example, microwave transmitter/receiver pair 16, 22 are mounted on support bases 42, 44 in a movable manner that permits the vertical height, Z, to be adjusted manually or by automatic means (e.g., by a motor and gear, drive belt, or hydraulically). This arrangement permits the detection system 10 to scan the microwave beam 21 up and down across the entire height of the tire's sidewalls 107, 109 (or container walls 100). Also illustrated in FIG. 6 (although not part of the invention) is a metallic band or ring 116, which can be used to support contraband 104 and hold it in place during driving, which reduces vibration and uneven wear of unbalanced tires. Vertically scanning the transmitter/receiver pair 16 and 22 up and down allows detection of a bag of contraband 104 that is much smaller than the inside dimensions (i.e., height, H) of tire cavity 102.

Figure 7:
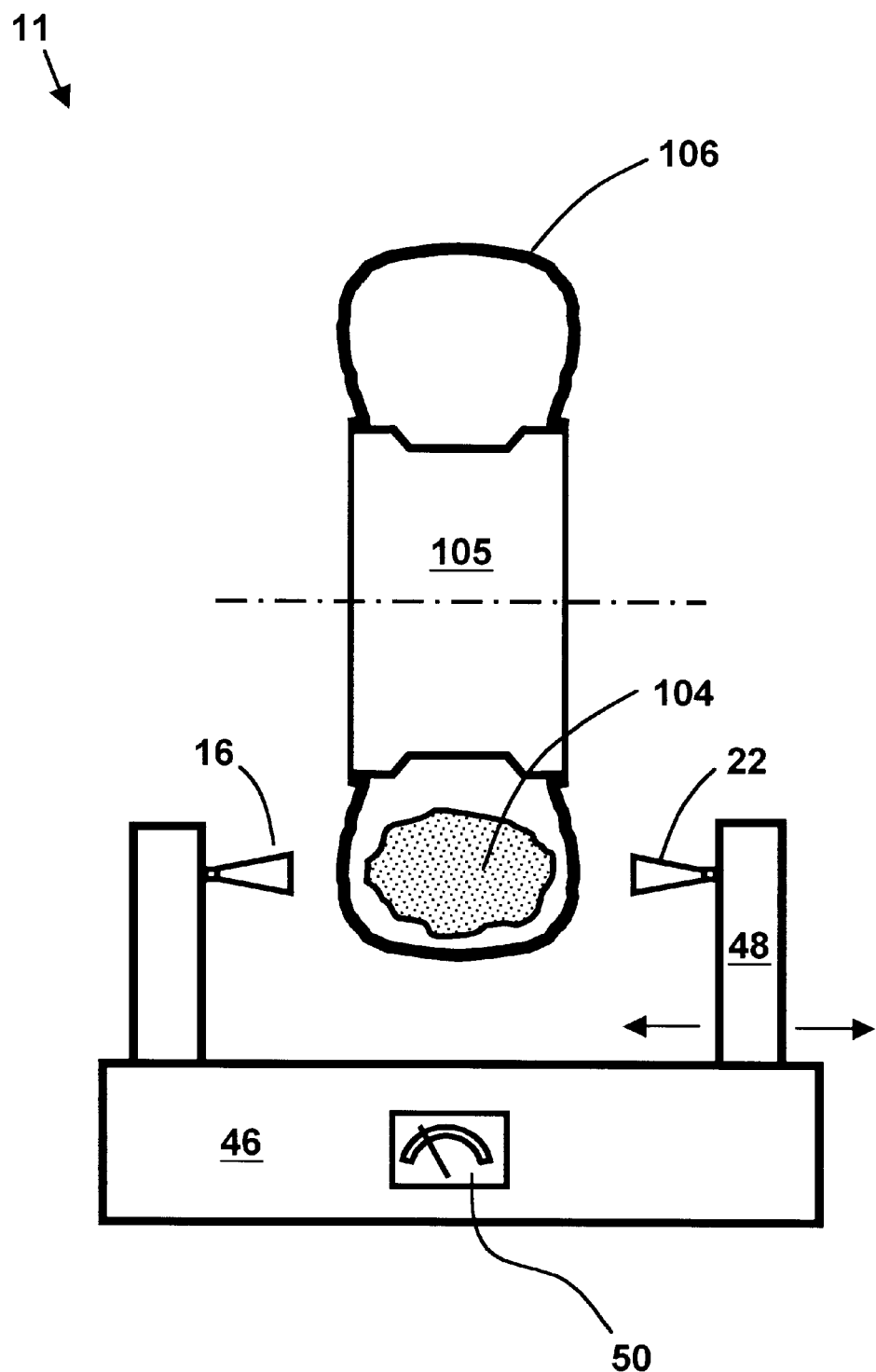
FIG. 7 illustrates a schematic side view of an ninth example of a system for detecting contraband hidden inside of a tire, according to the present invention.

FIG. 7 illustrates a schematic side view of a ninth example of a system for detecting contraband hidden inside of a tire, according to the present invention. In this example, transmitter 16 and receiver 22 are both mounted on a hand-held, portable frame 46. Frame 46 can include a display meter 50 to indicate the strength of the received microwave signal, or a LED display (not shown). Frame 46 comprises all of the required electronics, including power supply, oscillator, transmission line, detector, processor, etc. One of the two microwave horns (for example, receiver 22), can be mounted on a movable support post 48, which can be adjusted in and out to change the spacing between horns 16, 22 to accommodate one or more tires of varying widths and sizes. This hand-held, portable version of detection system 11 can be used for detecting contraband hidden in spare tires, or individual boxes, for example.

Figure 8:
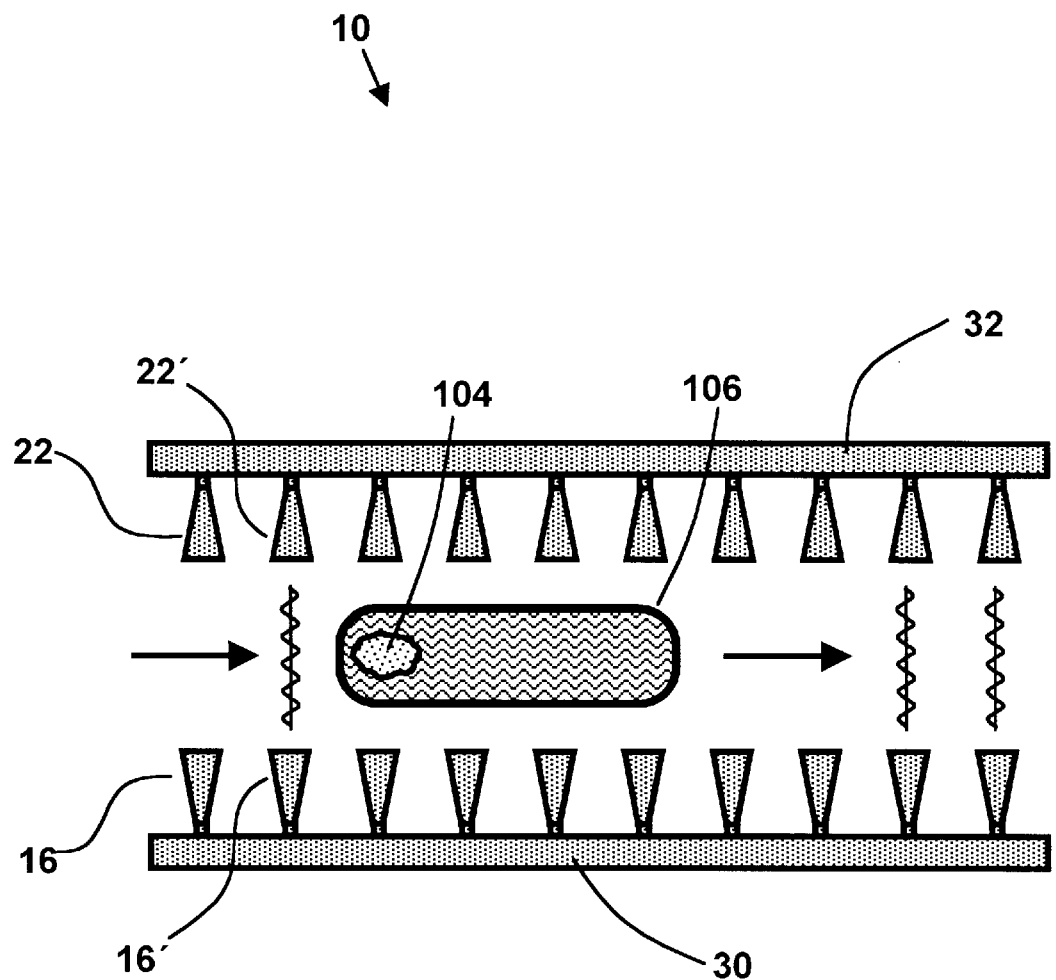
FIG. 8 illustrates a schematic plan view of a tenth example of a system for detecting contraband hidden inside of a tire, according to the present invention.

FIG. 8 illustrates a schematic plan view of a tenth example of a system for detecting contraband hidden inside of a tire, according to the present invention. In this example of a port of entry inspection station, a plurality of pairs of transmitter/receiver elements 16, 22 and 16', 22', are arranged to flank (i.e., straddle) a tire that rolls along the ground in-between two parallel rows of transmitters or receivers while the vehicle drives forward. All of the transmitters 16, 16', etc. can be mounted on a single support frame 30 (likewise for receivers 22, 22', etc. mounted on frame 32). This arrangement can detect an isolated, single bag of contraband 104 hidden inside of tire 106 (see FIGS. 4A and 4B) because the tire rotates relative to the array of detectors. Adjacent horns 16 and 16' can be different sized horns to provide a greater range of frequency coverage. The speed with which a vehicle can pass through the row of multiple horns is limited primarily by the safe driving speed (as determined by the spacing between transmitter 16 and receiver 22).

Figure 9:
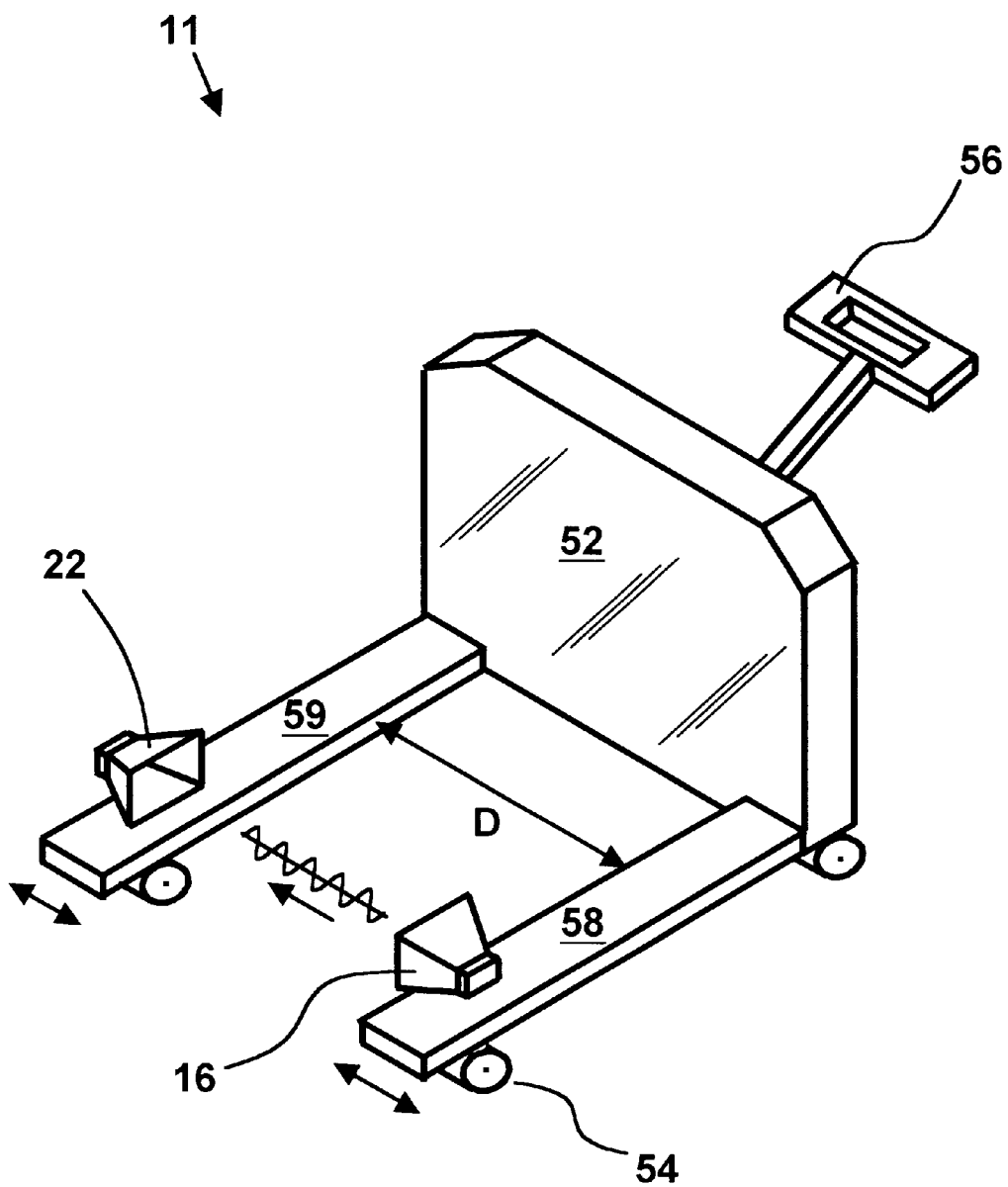
FIG. 9 illustrates a schematic isometric view of a eleventh example of a system for detecting contraband hidden inside of a tire, according to the present invention.

FIG. 9 illustrates a schematic isometric view of a eleventh example of a system for detecting contraband hidden inside of a tire, according to the present invention. In this example, transmitter/receiver pair 16, 22 are mounted on a wheeled "pallet mover" style transporter device 52. Transporter device 52 can be pushed with handle 56 and positioned underneath a large semi-tractor trailer rig. The spacing, D, between the two support forks 58 and 59 can be adjusted to accommodate a wide variation in tire sizes, single vs. double-axle tire configurations, etc. The main body of transporter device 52 can house the required electronics package, display, alarms, etc.

Figure 10:
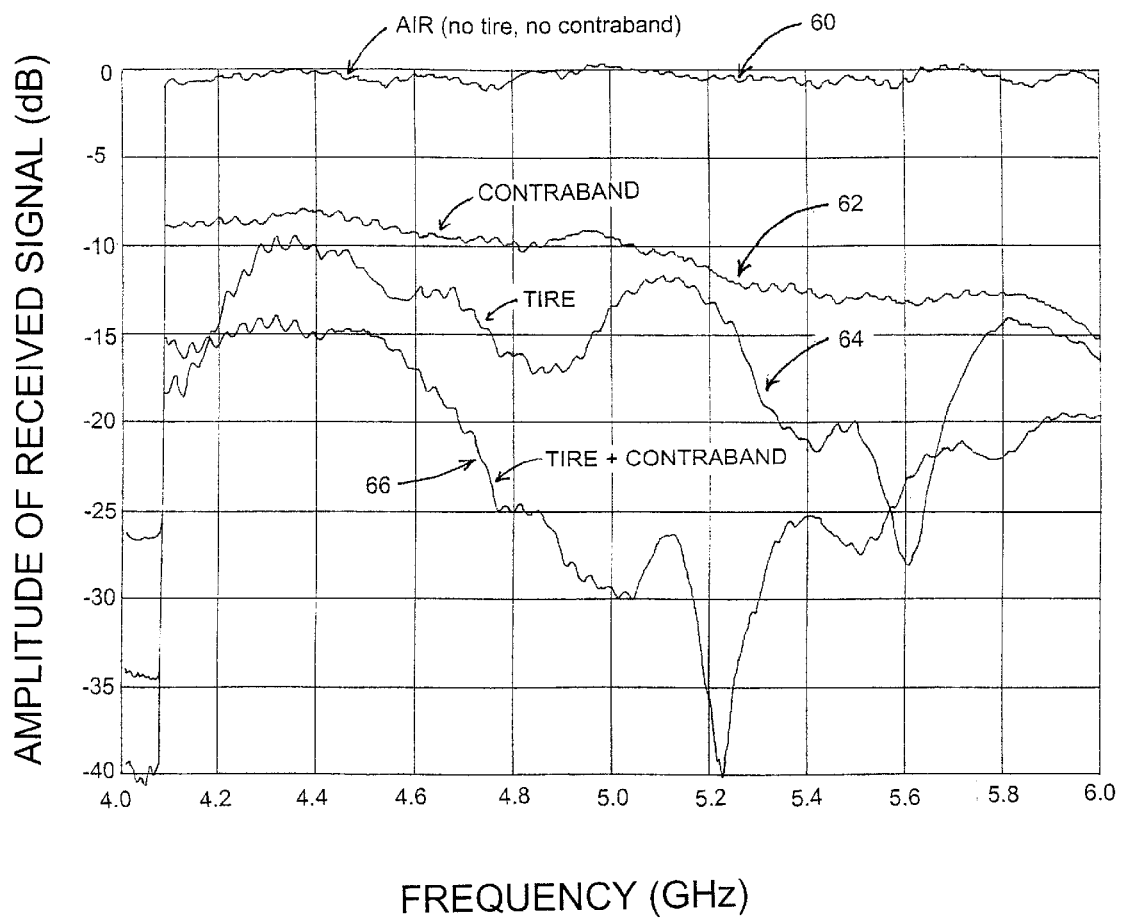
FIG. 10 illustrates experimental test data taken from an twelfth example of a system for detecting contraband hidden inside of a tire, according to the present invention.

FIG. 10 illustrates a set of experimental test data taken from a twelfth example of a system for detecting contraband hidden inside of a tire, according to the present invention. In this experiment, a steel-belted, radial automobile tire was used. A single 5 lb. plastic bag of flour (or sugar) was used to simulate a bag of cocaine (or heroin) and placed inside of the tire. Two identical standard gain waveguide horns 16, 22 (Narda #643, 4–6 GHz) were placed on opposite sides of the tire in a geometry that is similar to FIG. 2. A Wiltron Model 560A Scaler Network Analyzer (which includes the detector) and a Model 6647A Sweep Generator were used. FIG. 10 shows the amplitude of the received signal 20 (measured in dB) plotted against the applied frequency of the continuous (CW) microwave signal. Curve 60 shows the frequency response of only air (i.e., no tire, no contraband). Curve 62 shows the response for only the 5 lb. bag of simulated contraband, which indicates an attenuation of approximately −10 dB (relative to curve 60) due to absorption in the contraband. Curve 64 shows the attenuation due to only the tire, which is approximately −15 dB relative to the curve 60. Multiple resonances can be seen, particularly at 5.6 GHz, where increased attenuation occurs, possibly caused by enhanced absorption in the rubber sidewalls of the tire at those frequencies, or by multiple internal reflections, or both. Curve 66 illustrates the attenuation when the microwave radiation passes through both the tire and the simulated contraband hidden inside. In this case, the amount of attenuation varies from as low as −15 dB (at 4 GHz) to as high as −40 dB (at 5.2 GHz) relative to curve 60.

When compared relative to baseline curve 64 (tire only, no contraband), the tire plus contraband curve 66 has a maximum relative attenuation of −25 dB at 5.2 GHz. A large resonance absorption can be observed at 5.2 GHz, which provides the highest contrast and discrimination. It is important to note that the amount of attenuation is much larger than the noise in the signals. Clearly, the large attenuation values (more than −15 dB) measured in this experiment demonstrate the feasibility of detecting the presence of contraband hidden inside a tire.

The data show in FIG. 10 also support our belief that sweeping the frequency across a range of frequencies (e.g., 4–6 GHz) provides important information regarding the contents of the tire, useful for making an accurate decision regarding the presence of hidden contraband. An attenuation of about 17 dB corresponds to a power loss of a factor of 50, while a 30 dB attenuation corresponds to a power loss of a factor of 1000. A simple logic system can be designed that generates an audible or visual alarm when the power loss exceeds, for example, a factor of 200. The data shown in FIG. 10 was taken using a total radiated power of only 10 milliwatts; a level that poses no safety hazard to the operator or to the public.

Figure 11:
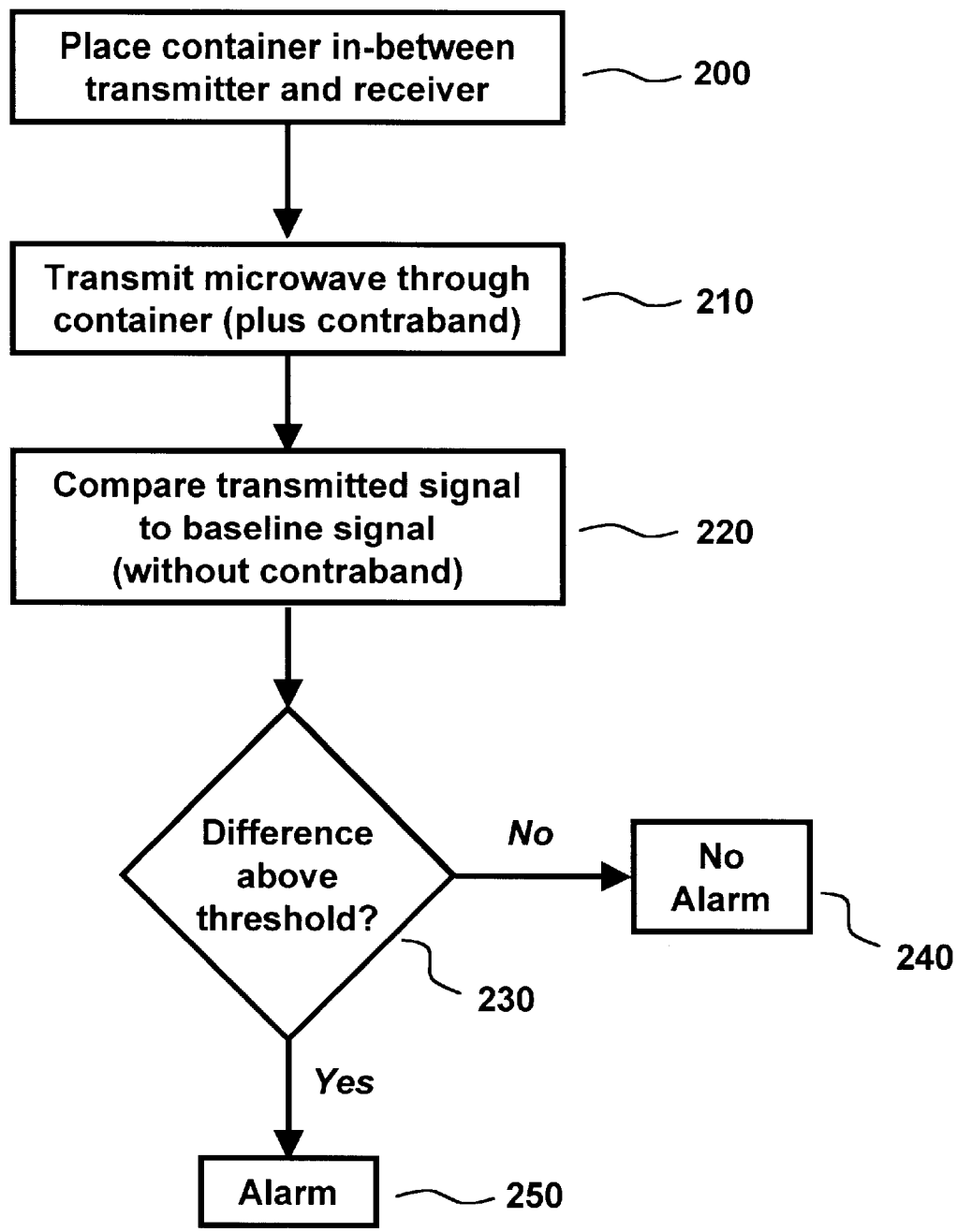
FIG. 11 illustrates a thirteenth example of a method for detecting contraband hidden inside of a tire, according to the present invention.

FIG. 11 illustrates a thirteenth example of a method for detecting contraband hidden inside of a tire, according to the present invention. In step 200, a container is placed in-between a microwave transmitter and receiver. In step 210, a test microwave signal is launched from the transmitter and subsequently received by the receiver. Then, in step 220, the received signal is analyzed by a processor for characteristic properties, such as amplitude, speed, time delay, phase, and disappearance. Next, in step 230, the processor compares the received test microwave signal to a baseline received signal that is stored in a library or its memory. The baseline signal represents the situation where container does not have contraband hidden inside, or contains normal contents. A decision is made by processor in step 230 whether or not the received test signal is sufficiently different than the baseline signal to activate an alarm or alert the operator in step 250 (visual, audible, etc.) indicating the presence of abnormal contents inside the container, such as hidden contraband.

For continuous wave microwave generation (i.e., frequency-domain system), the processor in step 230 can compare the amplitude of the received signal to the known amplitude of the baseline signal. This method can include sweeping the frequency across a limited band of frequencies (e.g., from 4–6 GHz). Alternatively, in step 230, the phase of the received signal may be compared to both the launched signal, and to the phase of the received baseline signal, useful for indicating the presence of contraband.

For pulsed operation (i.e., time-domain system), the oscillator generates one or more short pulses or bursts of microwave radiation (e.g. 600 ps pulse duration). The receiver, detector, and processor measure the time period for the pulse to reach the receiver after passing through the container (i.e., time-of-flight). If the container has hidden contraband (as opposed to empty space), then the arrival time of the pulse will be delayed by passing through the contraband. The delay in the arrival time (i.e., the difference in the measured time-of-flight between the received signal and the baseline signal) can be measured with appropriate ultra-fast electronics. If the delay is too large, this indicates the suspected presence of contraband, and the processor can then active an alarm. For pulsed operation, the transmitter and receiver elements can be wideband in nature. The processor can also analyze the transmitted pulse of microwave energy for attenuation of the amplitude. The processor can combine information about both the attenuation and the time delay of the transmitted pulses to make a more reliable prediction of possible hidden contraband.

Referring to FIG. 3, the method of the present invention can comprise transmitting microwave radiation through two or more adjacent containers (e.g., two adjacent tires).

Referring to FIG. 4A, the method of the present invention can comprise transmitting microwave radiation through a tire that is being rotated past a fixed transmitter/receiver pair. Conversely (not shown), the transmitter/receiver pair can be rotated around a fixed tire. In more general terms, the transmitter/receiver pair can be scanned in many different directions about the container, particularly if the size of the transmitter/receiver elements (e.g., horns) are much smaller than the container. This is illustrated in FIG. 6, which shows the transmitter/receiver pair being scanned up and down in the vertical direction along the sidewall of a tire. Alternatively, a portable, hand-held unit can be manually moved about the container, as illustrated in FIG. 7. Because the distance between the container and the transmitter/receiver pair is not critical in the present invention, this makes it easy move a hand-held unit around a tire, for example, without having to worry about keeping a precise distance from the tire's surface.

Referring to FIG. 4B, the method of the present invention can comprise transmitting a plurality of different microwave beams through a container from a plurality of transmitter/receiver pairs, whereas each beam has a different frequency than the adjacent beam. Each beam can be transmitted simultaneously, or at different sequential times, depending on the application, and operation mode (i.e., frequency-domain, time-domain, etc.).

Referring to FIG. 8, the method of the present invention can comprise rolling the tire (or rotating the container on a turntable, for example) through a fixed array of multiple pairs of transmitter/receiver units. This can be useful for detecting a single bag of contraband hidden inside of a tire, for example, without having to stop the vehicle.

Referring to FIG. 9, the method of the present invention can comprise pushing or maneuvering a portable detection system mounted on a wheeled dolly or transporter device into position, and, possibly, adjusting the spacing between two support arms (e.g., forks 58, 59) to accommodate one or more tires or containers of varying sizes.

Figure 12A:
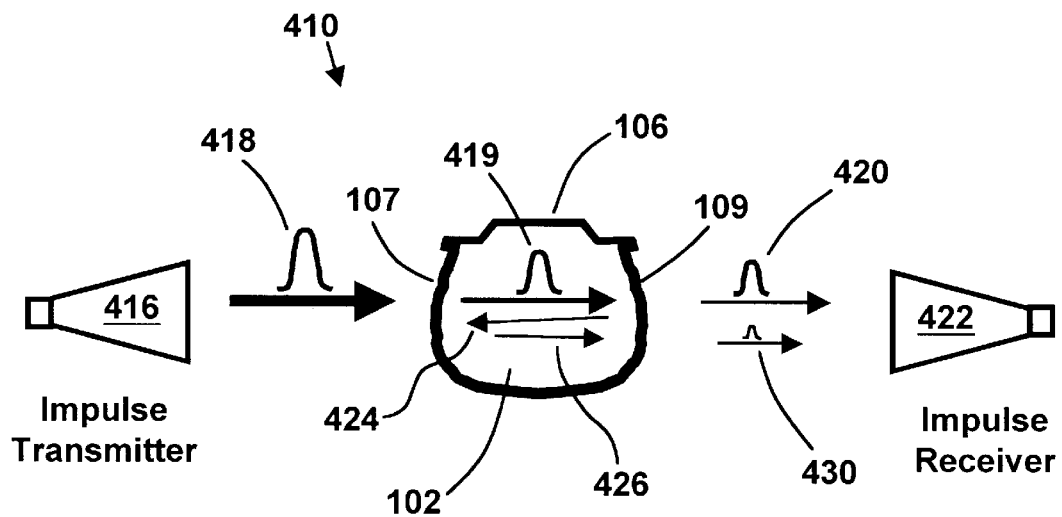
FIG. 12A illustrates a fourteenth example of a method for detecting contraband hidden inside of a tire, according to the present invention.

FIG. 12A illustrates a fourteenth example of a method for detecting contraband hidden inside of a tire, according to the present invention. In this example, the invention utilizes a time-domain system. Impulse transmitter 416 transmits an ultrashort pulse of microwave energy 418 towards tire 106. The duration of test pulse 418 can be in-between 5 ps and 100 ns. Preferably the pulse width is approximately 600 ps, which corresponds roughly to the time delay expected to be caused by the presence of contraband 104 hidden inside a tire. In FIG. 12A the tire's cavity 102 is empty; i.e., no contraband is present. Microwave pulse 418 passes through front wall 107, then enters cavity 102, wherein some of pulse 419 passes through back wall 109 of tire 106. After passing through back wall 109, direct pulse 420 is received by impulse receiver 422 (and analyzed by associated processing equipment, not shown).

Additionally, some of pulse 418 reflects off of the inner surface of back wall 109. This first reflected pulse 424 then travels back towards the inner surface of front wall 107, whereupon it reflects again. The second reflected pulse 426 travels towards back wall 109. After passing through back wall 109, first echo pulse 430 is received by receiver 422. Because the echo pulse 430 travels a longer total path (due to multiple internal reflections), the arrival time of echo pulse 430 is delayed relative to the arrival time of direct pulse 420. In a similar fashion., multiple echo pulses (i.e., second echo pulse, third echo pulse, etc.) may also be detected by receiver 422, depending on the degree of attenuation by the tire's walls and the sensitivity of the detection system's electronics.

Figure 12B:
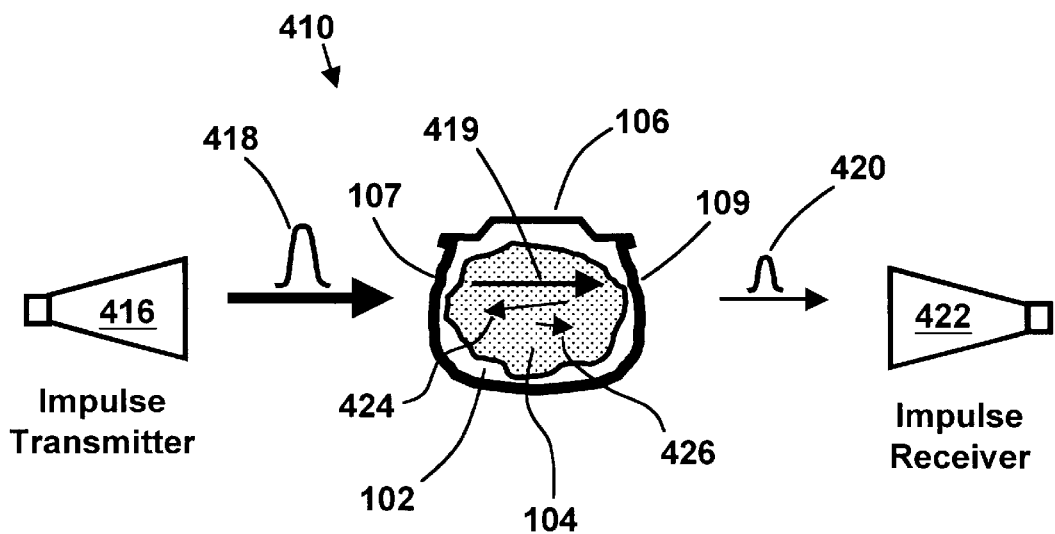
FIG. 12B illustrates a fifthteenth example of a method for detecting contraband hidden inside of a tire, according to the present invention.

FIG. 12B illustrates a fifthteenth example of a method for detecting contraband hidden inside of a tire, according to the present invention. In this example, the method is similar to that described for FIG. 12A, except that tire 106 now contains contraband 104. The presence of contraband 104 attenuates the amplitude of pulse 418 (and slows down the speed of pulse 418) as it passes through contraband 104. FIG. 12B illustrates that some of pulse 419 passes through back wall 109, while some of pulse 419 reflects off of walls 109 and 107 to form first reflected pulse 424 and second reflected pulse 426, respectively. However, due to the possibly strong attenuation by contraband 104, the magnitude of second reflected pulse 426 might be so weak that after passing finally through back wall 109, it is too weak to be detected by receiver 422. The lack of a detectable first echo pulse 430 (as compared to the situation in FIG. 12A, where echo pulse 420 is strong enough to be detected), or a substantial extra delay in time, can provide a useful indication of the presence of hidden contraband.

Figure 13A:
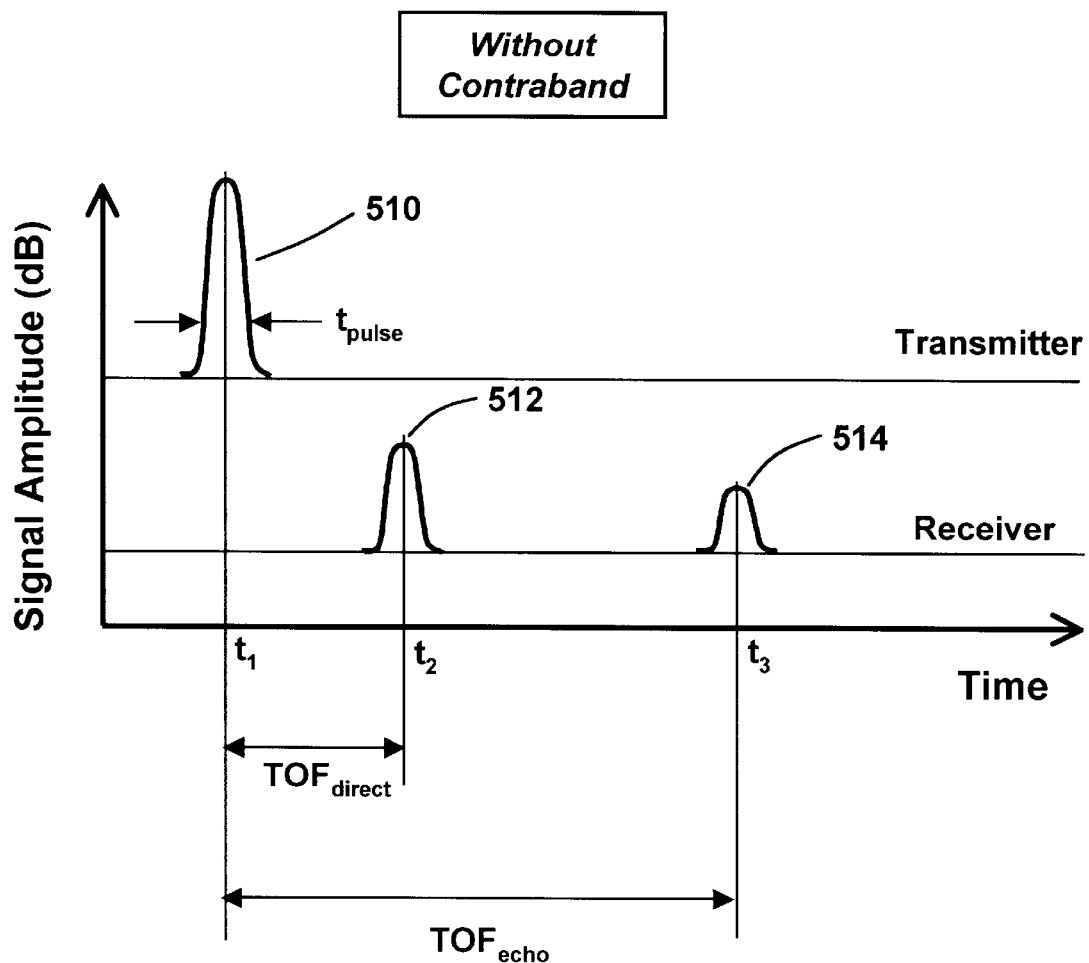
FIG. 13A illustrates a sixteenth example of a method for detecting contraband hidden inside of a tire, according to the present invention.

FIG. 13A illustrates a sixteenth example of a method for detecting contraband hidden inside of a tire, according to the present invention. In this example, tire 106 is empty (i.e., without contraband). Referring also to FIG. 12A, microwave pulse 510, having a pulse width equal to $t_{pulse}$, is launched towards tire 106 at time=$t_1$. Note that $t_{pulse}$ can be approximately 600 ps. Direct pulse 512 is received later at time=$t_2$. The direct time-of-flight (TOF$_{direct}$) from transmitter 416 to receiver 422 is given by equation (1):

$$TOF_{direct}=t_2-t_1 \quad (1)$$

Subsequently, after two internal reflections, first echo pulse 430 is received at time=$t_3$. The echo time-of-flight (TOF$_{echo}$) of first echo pulse 430 from transmitter 416 to receiver 422 is given by equation(2):

$$TOF_{echo}=t_3-t_1 \quad (2)$$

As discussed before, multiple subsequent echo pulses may be detected after detecting the first echo pulse, depending on the sensitivity of the detection equipment.

Figure 13B:
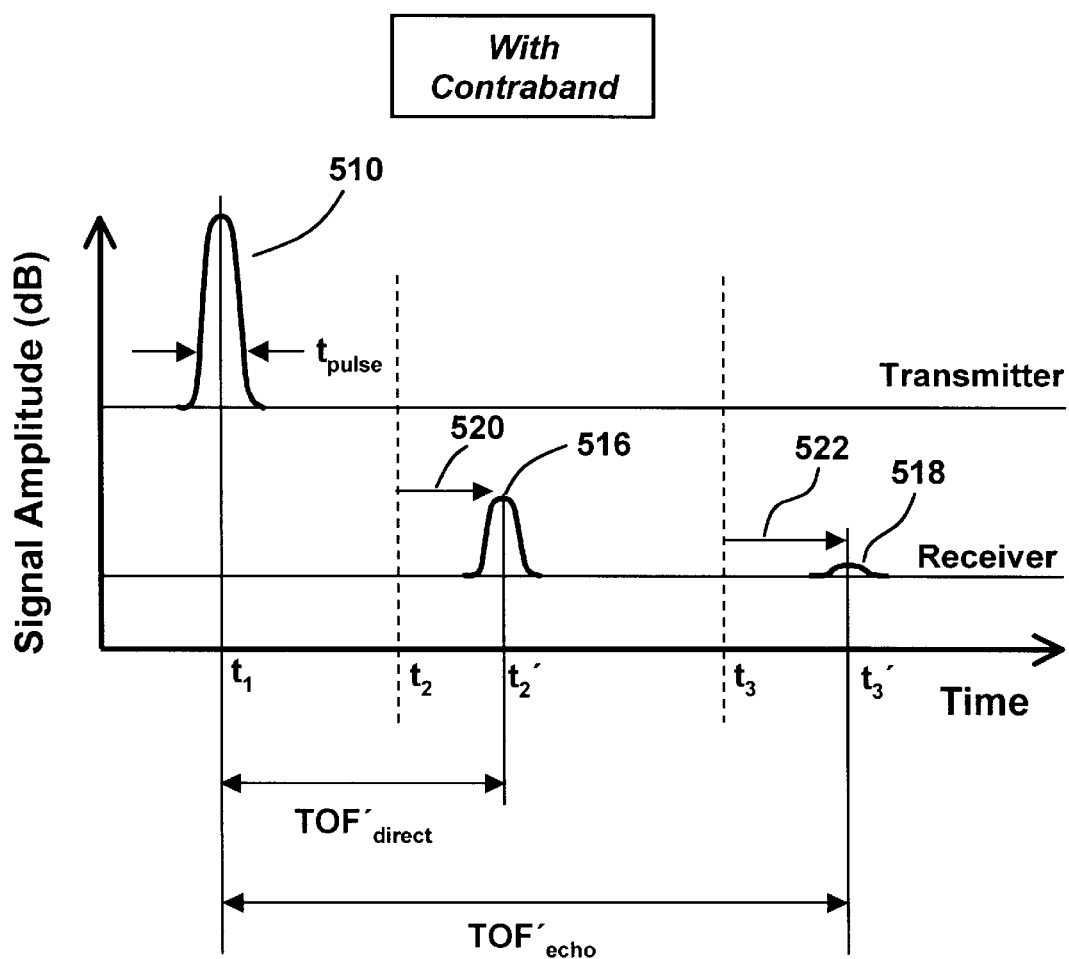
FIG. 13B illustrates a seventeenth example of a method for detecting contraband hidden inside of a tire, according to the present invention.

FIG. 13B illustrates a seventeenth example of a method for detecting contraband hidden inside of a tire, according to the present invention. In this example, tire 106 is filled with hidden contraband 104. Referring also to FIG. 12B, microwave pulse 510, having a pulse width equal to $t_{pulse}$, is launched towards tire 106 at time=$t_1$. Direct pulse 516 is received later at time=$t_2'$. The direct time-of-flight (TOF'$_{direct}$) from transmitter 416 to receiver 422 is given by equation (3):

$$TOF'_{direct}=t_2'-t_1 \quad (3)$$

Subsequently, after two internal reflections, first echo pulse 518 (if detectable) is received at time=$t_3'$. The echo time-of-flight (TOF'$_{echo}$) of first echo pulse 430 from transmitter 416 to receiver 422 is given by equation (4):

$$TOF'_{echo}=t_3'-t_1 \quad (4)$$

If the attenuation of microwave pulse 418 is sufficiently strong as the pulse passes through contraband 104 a total of three times (i.e., three passes), then first echo pulse 518 may not be detectable by receiver 422 after finally passing through back wall 109. Active monitoring of receiver 422 can detect the disappearance of first echo pulse 430, which would indicate the presence of hidden contraband. A simple YES/NO logic circuit can be used to detect this event.

Additional information can be derived by analyzing the arrival times of these pulses. Referring still to FIGS. 13A and 13B, the passage of pulse 510 through contraband 104 slows down the speed of pulse 516, which increases the direct time-of-flight, TOF'$_{direct}$. The difference (i.e., time delay $\Delta$TOF$_{direct}$ 520) between the measured time-of-flight, TOF'$_{direct}$ (i.e., with contraband) and the baseline time-of-flight, TOF$_{direct}$ (i.e., without contraband), can also provide a useful indication of the presence of contraband. For example, with a tire width of 10 cm, and a relative dielectric constant of 3 for the contraband, the time delay $\Delta$TOF$_{direct}$ is approximately equal to 600 ps. Consequently, if the calculated time delay $\Delta$TOF$_{direct}$ is greater than a predetermined or pre-set threshold value (e.g., 100 ps), this would indicate the presence of hidden contraband. Such a time delay 520 (i.e., 600 ps) is easily measured using a 20 GHz oscilloscope, where the inherent time difference is approximately 5 ps. The time delay $\Delta$TOF$_{direct}$ is given by equation (5):

$$\Delta TOF_{direct}=TOF'_{direct}-TOF_{direct} \quad (5)$$

A comparison of equations (1) and (3) shows that an equivalent expression for $\Delta$TOF$_{direct}$ is given by equation (6):

$$\Delta TOF_{direct}=t_2'-t_2 \quad (6)$$

Alternatively, if the attenuation of contraband 104 is not as strong, a first echo pulse 518 may actually be detectable. In this case, the time delay 522 of first echo pulse 518 (i.e., the difference $\Delta$TOF$_{echo}$ between the measured time-of-flight, TOF'$_{echo}$ (i.e., with contraband) and the baseline time-of-flight, TOF$_{echo}$ (i.e., without contraband)), may also provide a useful indication of the presence of contraband. The time delay $\Delta$TOF$_{echo}$ is given by equation (7):

$$\Delta TOF_{echo}=TOF'_{echo}-TOF_{echo} \quad (7)$$

Likewise, a similar comparison of equations (3) and (4) shows that an equivalent expression for $\Delta$TOF$_{echo}$ is given by equation (8):

$$\Delta TOF_{echo}=t_3'-t_3 \quad (8)$$

Figure 14:
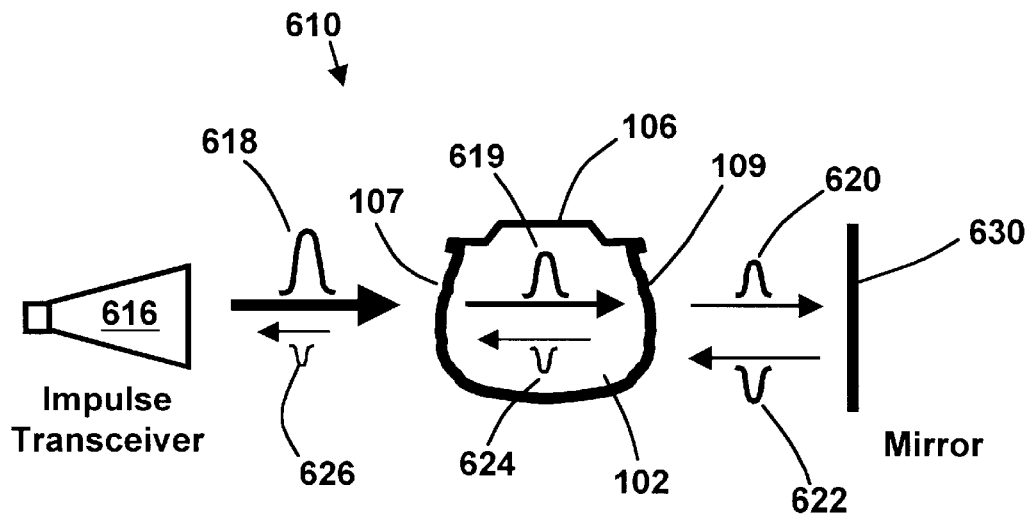
FIG. 14 illustrates an eighteenth example of an apparatus and method for detecting contraband hidden inside of a tire, according to the present invention.

FIG. 14 illustrates an eighteenth example of an apparatus and method for detecting contraband hidden inside of a tire, according to the present invention. In this example of a time-domain system 610, impulse transceiver 616 launches a microwave pulse 618 towards tire 106. Pulse 619 travels through the empty cavity 102 of tire 106, and then passes through back wall 109, ultimately exiting into free space as pulse 620. Disposed on the opposite side of tire 106 is mirror 630, which is oriented substantially perpendicular to the direction of travel of pulse 618. Mirror 630 reflects substantially all of pulse 620 back towards transceiver 616 as reflected pulse 622. Mirror 630 is a metal reflecting surface specifically designed to reflect microwave energy, and can be a flat sheet of conducting metal (e.g., aluminum or copper) or a thin coating of conductive metal applied to a non-conducting substrate. Alternatively, mirror 630 can be a corner-reflecting cube (not illustrated). Reflected pulse 622 enters tire 106 through wall 109, passes through empty cavity 102, and passes through wall 107, exiting into free space as pulse 626. Transceiver 616 receives pulse 626 sometime after pulse 618 was launched. The time-of-flight (TOF) of pulse 618, 626 depends-on the distance traveled, and any retardation due to the walls of tire 106. In this example, mirror 630 replaces the receiver unit 422 shown in FIGS. 12A and 12B. Replacing receiver 422 with mirror 630 can simplify the operation of detection system 610, since mirror 630 can be a thin sheet of metal, and hence, takes up less space than receiver 422. Mirror 630 can be mounted to the ground 108 (not shown), either permanently (e.g., at an inspection station), or temporarily (e.g., at a checkpoint). Alternatively, mirror 630 may comprise the sheet metal wall of an automobile, wherein tire 106 can be a spare tire mounted to the automobile in front of the sheet metal wall. Mirror 630 can also replace the receiver horn 22 in a hand-held portable unit 46 (shown in FIG. 7), which reduces the size of portable detector 46; making it more compact and easier to use.

Figure 15:
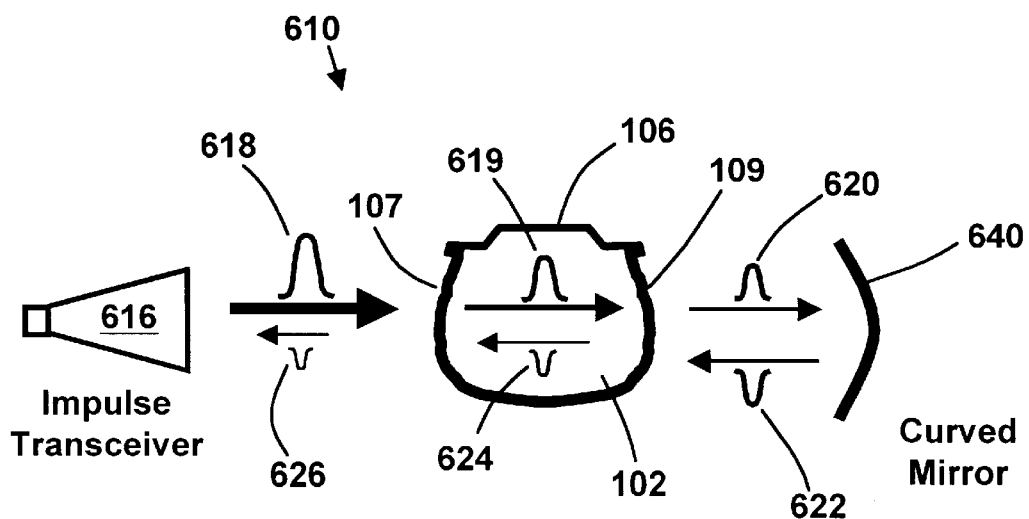
FIG. 15 illustrates a nineteenth example of an apparatus and method for detecting contraband hidden inside of a tire, according to the present invention.

FIG. 15 illustrates a nineteenth example of an apparatus and method for detecting contraband hidden inside of a tire, according to the present invention. In this example, reflective mirror 640 is curved to focus the reflected microwave pulse 622 back towards transceiver 616. Curved mirror 640 can have a parabolic shape. By focusing the reflected pulse 622, reception efficiency of transceiver 616 can increase, since spillover of the microwave radiation is reduced.

Figure 16:
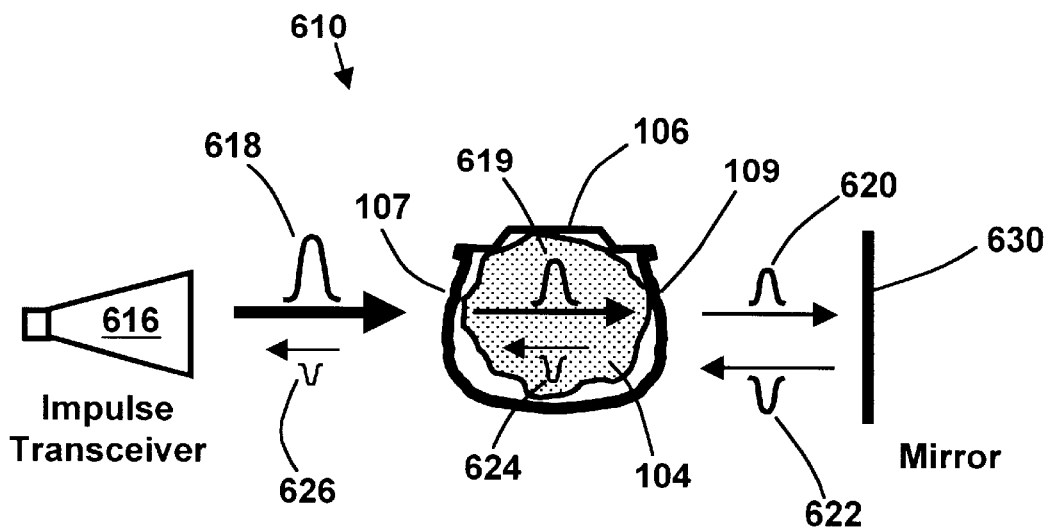
FIG. 16 illustrates a twentieth example of an apparatus and method for detecting contraband hidden inside of a tire, according to the present invention.

FIG. 16 illustrates a twentieth example of an apparatus and method for detecting contraband hidden inside of a tire, according to the present invention. In this example of a time-domain system 610, impulse transceiver 616 launches a microwave pulse 618 towards tire 106. Pulse 619 travels through the tire, which is filled with contraband 104, then passes through back wall 109, exiting into free space as pulse 620. Disposed on the opposite side of tire 106 is mirror 630, which is oriented substantially perpendicular to the direction of travel of pulse 618. Mirror 630 reflects substantially all of pulse 620 as reflected pulse 622. Reflected pulse 622 enters tire 106 through wall 109, passes a second time (i.e., two-pass) through contraband 104, and (assuming that pulse 624 hasn't been completely attenuated by two passes through contraband 104) passes through wall 107, exiting into free space as pulse 626. Transceiver 616 receives pulse 626 sometime after pulse 618 was launched. The time-of-flight (TOF) of pulse 618, 626 depends on the distance traveled, and any retardation due to the walls of tire 106 and hidden contraband 104.

Using detection system 610, the difference between the time-of-flight for the pulse traversing twice across a tire without contraband (i.e. the baseline TOF), and the measured TOF for the tire with suspected contraband, can provide a useful signal indicative of the presence of contraband.

Figure 17:
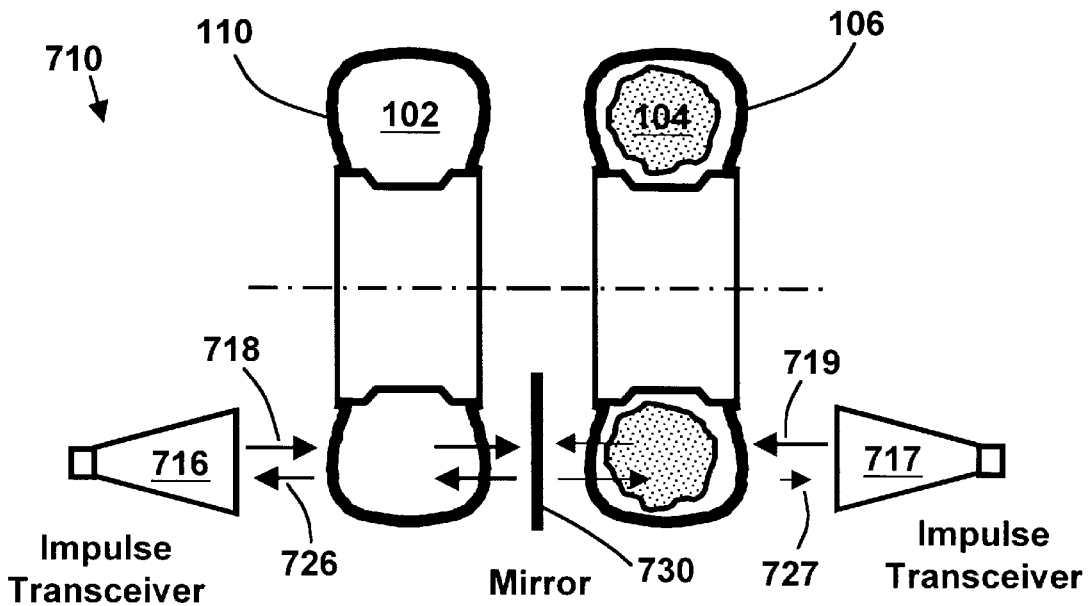
FIG. 17 illustrates a twenty-first example of an apparatus and method for detecting contraband hidden inside of a tire, according to the present invention.

FIG. 17 illustrates a twenty-first example of an apparatus and method for detecting contraband hidden inside of a tire, according to the present invention. In this example of a time-domain system 710, two tires 106 and 110 are disposed closely adjacent to each other with only a small gap in-between, for example, in a double-axle, double-tire truck arrangement. Mirror 730 is disposed in-between the two tires, e.g., between tire 110 and 106. Mirror 730 can be a flat sheet of conductive metal. Impulse transceiver 716 launches a microwave pulse 718 towards tire 110, which passes through empty cavity 102, reflects from mirror 730, then passes through empty cavity 102 a second time, and finally is received by transceiver 716. As before, the time-of-flight for the pulse is measured. Likewise, on the right-hand side, transceiver 717 launches pulse 719 towards closely-adjacent tire 106, which passes through contraband 104, then reflects from mirror 730, then passes through contraband 104 a second time, and finally is received by transceiver 717. In this case, the time-of-flight is longer, which indicates the presence of hidden contraband.

Figure 18:
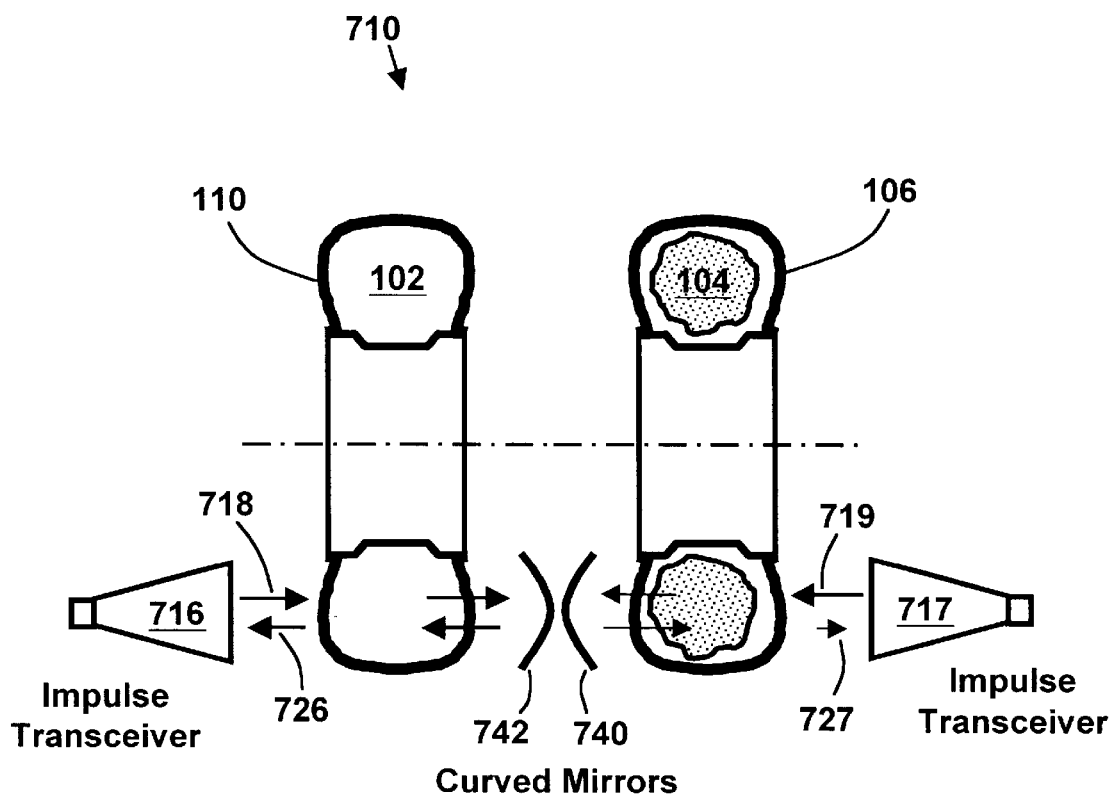
FIG. 18 illustrates a twenty-second example of an apparatus and method for detecting contraband hidden inside of a tire, according to the present invention.

FIG. 18 illustrates a twenty-second example of an apparatus and method for detecting contraband hidden inside of a tire, according to the present invention. In this example, mirror 730 from FIG. 17 has been separated into two adjacent mirrors 740 and 742, disposed to reflect the pulses from transceiver 717 and 716, respectively. Alternatively, mirrors 740 and 742 can be curved to focus the microwave radiation, as shown in FIG. 18. Mirrors 740 and 742 can be joined into a single, integrated unit (not illustrated).

The particular examples discussed above are cited to illustrate particular embodiments of the invention. For example, the time-domain system illustrated in FIGS. 12A, 12B, 13A, and 13B can be modified to repeatedly generate a series of substantially identical microwave pulses, with a repetition rate of between, for example, 1 KHz and 1 MHz, (although other repetition rates could be used). Alternatively, a frequency-domain system can be used for the operation of the detection system illustrated in FIGS. 14–18. Superposition of a launched CW microwave with the received CW microwave inside of a single transceiver unit can create unique interference phenomena, including phase interference effects that can provide useful information for determining the presence of hidden contraband. Other applications and embodiments of the apparatus and method of the present invention will become evident to those skilled in the art.

The actual scope of the invention is defined by the claims appended hereto.

We claim:

1. An inspection system for inspecting a non-metallic container having unknown contents, comprising:
    transmitting means, disposed on one side of the container, for launching a test microwave signal towards the container;
    receiving means, disposed on the opposite side of the container, for receiving the launched test microwave signal after having passed through the container;
    processing means for detecting, analyzing, and comparing at least one characteristic property of the received test microwave signal with the same characteristic property of a received baseline microwave signal generated by passing a baseline microwave signal through a substantially similar container having normal contents; and
    alerting means, in operative association with said processing means, for indicating the presence of abnormal contents within the container, based on results of the comparison of the test signal with the baseline signal;
    wherein the launched microwave signal comprises a pulse of microwave radiation;
    wherein the processing means comprises a timer capable of measuring the time-of-flight of a microwave pulse as it travels from the transmitter means to the receiver means; and
    wherein the characteristic property of the received signal comprises the time-of-flight of the microwave pulse measured as it travels from the transmitting means, through the container, to the receiving means.

2. The system of claim 1, further comprising a microwave oscillator for generating microwave radiation.

3. The system of claim 2, further comprising a power supply operatively connected to the oscillator.

4. The system of claim 1, further comprising a detector for converting the received microwave signal into a voltage signal.

5. The system of claim 1, wherein the transmitting and receiving means comprise a standard gain waveguide horn.

6. The system of claim 1, wherein the duration of the microwave pulse is between approximately 5 ps and 100 ns.

7. The inspection system of claim 6, wherein the duration of the ultra-short microwave pulse is greater than about 5 ps; and wherein the duration of the ultra-short microwave pulse is less than about 600 ps.

8. The system of claim 1, wherein the launched microwave signal comprises a series of repeated short pulses.

9. The system of claim 1, wherein the transmitting means and receiving means comprises a plurality of different sized transmitter horns and receiver horns, wherein each horn is optimized for a standard gain within a unique range of frequencies.

10. The inspection system of claim 1, further comprising:
    an impulse transmitter connected via a first transmission line to an ultra-short microwave pulser;
    an impulse receiver connected via a second transmission line to the timer, wherein the timer is operatively associated with a processor;
    a pickoff disposed in the first transmission line in-between the pulser and the transmitter, for diverting a small amount of pulsed microwave energy from the first transmission line; and a trigger module, operatively associated with the pickoff, for receiving the small amount of pulsed microwave energy diverted by the pickoff;

wherein the trigger module delivers a trigger signal to the timer in response to the pulse of microwave energy received from the pickoff; and wherein the timer detects the time at which the pulse is received by the impulse receiver, relative to the time when the pulse was launched by the pulser, via the trigger signal.

11. The inspection system of claim 1, wherein the difference between the time at which the pulse is received by the impulse receiver and the time when the pulse was launched by the pulser equals the Time-of-Flight (TOF) of the microwave pulse as it travels from the transmitter to the receiver;

wherein the characteristic property of the received test microwave signal comprises the Time-of-Flight of the received test microwave signal; and wherein the characteristic property of the received baseline microwave signal comprises the Time-of-Flight of the received baseline microwave signal; and wherein the processor compares the Time-of-Flight of the received test microwave signal with the Time-of-Flight of the received baseline microwave signal and determines if the container contains any contraband or abnormal contents.

12. The inspection system of claim 1, further comprising a power supply for providing 1 watt or less of electric power to the transmission means.

13. The inspection system of claim 1, wherein the total radiated power of the transmitting means is less than or equal to 10 milliwatts; a level that poses no safety hazard to people.

14. An inspection system for inspecting a tire mounted on a vehicle, the tire possibly containing hidden contraband, comprising:

transmitting means, disposed on one side of the tire, for launching a test microwave signal towards the tire;

receiving means, disposed on the opposite side of the tire, for receiving the launched test microwave signal after having passed through the tire; and processing means for detecting, analyzing, and comparing at least one characteristic property of the received test microwave signal with the same characteristic property of a received baseline microwave signal generated by passing a baseline microwave signal through a substantially similar tire without contraband hidden inside; and alerting means, in operative association with said processing means, for indicating the presence of contraband hidden within the tire, based on results of the comparison of the test signal with the baseline signal;

wherein the transmitting means and the receiving means are coaxially aligned and diametrically opposed to one another on opposite sides of the tire; and are positioned so that a microwave signal launched by the transmitting means passes through at least both sidewalls of the tire before being received by the receiving means.

15. The system of claim 14, wherein the transmitted microwave signal is continuously generated at a fixed frequency selected from approximately 8 to 12 GHz.

16. The system of claim 14, further comprising means for sweeping the frequency of the transmitted microwave signal between a minimum and maximum frequency.

17. The system of claim 16, wherein the minimum frequency is approximately 4 GHz, and the maximum frequency is approximately 6 GHz.

18. The system of claim 14, wherein the characteristic property of the received signal comprises the amplitude of the received signal.

19. The system of claim 14, wherein the characteristic property of the received signal comprises the phase of the received signal.

20. The system of claim 14, wherein the transmitting means and the receiving means are mounted on the ground.

21. The system of claim 20, further comprising means for rotating the tire during inspection while the vehicle is parked.

22. The inspection system of claim 20:

wherein the means for rotating the tire during inspection while the vehicle is parked comprises a pair of rollers that supports the tire during rotation;

wherein the rollers are mounted in a well recessed below the ground; and wherein the system comprises as many wells containing pairs of rollers as there are rotatable tires mounted on the vehicle; and wherein each roller comprises a motor for rotating each roller, whereby tires that are unpowered and freewheeling can be forcibly rotated.

23. The system of claim 14, further comprising a protective radome structure covering the transmitting means, the receiving means, or both together.

24. The system of claim 14, further comprising movable scanning means for adjusting the vertical position of both the transmitting and receiving means, relative to the tire.

25. The system of claim 14, wherein the transmitting means, receiving means, and processing means are packaged as a hand-held, portable unit.

26. The hand-held, portable unit of claim 25, wherein the distance between the transmitting means and the receiving means is adjustable, to accommodate one or more tires of varying width.

27. The system of claim 14, further comprising two parallel rows of transmitters and receivers, comprising a transmitting row having a plurality of transmitting means aimed to launch microwave signals in a direction perpendicular to the direction of the tire's travel while the vehicle is moving; and further comprising a receiving row having a plurality of receiving means aimed to receive the corresponding transmitted microwave signals; wherein the rows are sufficiently long to permit inspection of at least one complete revolution of the tire.

28. The system of claim 14, wherein the transmitting means, receiving means, and processing means are mounted on a movable transporter device, wherein the device has means for adjusting the distance between the transmitting means and the receiving means to accommodate one or more tires of varying sizes.

29. The inspection system of claim 14, wherein the transmitted microwave signal is generated at a frequency of 5.8 GHZ, which corresponds to a Special ISM (Instrument, Scientific, and Medical) fixed frequency that doesn't require special approval of an operating license.

30. The inspection system of claim 14, wherein the transmitted microwave signal is generated at a frequency of about 10 GHZ, which allows the system to be constructed using commercially available off-the-shelf components that are used in radar speed guns operating in the X-band at about 10 GHZ.

31. The inspection system of claim 14, wherein the total radiated power of the transmitting means is less than or equal to 10 milliwatts; a level that poses no safety hazard to people.

32. An inspection system for inspecting a first non-metallic container having unknown contents, comprising:

first transceiver means, disposed on one side of the first container, for launching a test microwave signal towards the first container, and for receiving the microwave signal from the first container;

reflecting means, disposed on the opposite side of the first container, for reflecting the launched test microwave signal after having passed through the first container back towards the first transceiver, wherein the microwave signal received by the first transceiver means has passed through the container two times;

first processing means for detecting, analyzing, and comparing at least one characteristic property of the received test microwave signal with the same characteristic property of a received baseline microwave signal generated by passing a baseline microwave signal two times through a substantially similar container having normal contents; and first alerting means, in operative association with said first processing means, for indicating the presence of abnormal contents within the first container, based on results of the comparison of the test signal with the baseline signal.

33. The system of claim 32, wherein the reflecting means comprises a flat sheet of conductive metal.

34. The system of claim 32, wherein the reflecting means comprises a curved sheet of conductive metal, for focusing the microwave signal on to the first transceiver means.

35. The system of claim 32, wherein the reflecting means is disposed in-between the first container and a second, closely-spaced, adjacent container.

36. The system of claim 35, wherein the two containers comprise two closely-spaced, adjacent tires mounted on a vehicle.

37. The system of claim 35, further comprising a second transceiver means disposed on the opposite side of the second container, disposed for launching a second test microwave signal towards the second container, and for receiving the second test microwave signal from the second container, after reflecting from the reflecting means; and further comprising second processing means for detecting, analyzing, and comparing at least one characteristic property of the second received microwave signal with the same characteristic property of a second received baseline microwave signal generated by transmitting a second baseline microwave signal through the second container without contraband hidden inside; and second alerting means indicating the presence of hidden contraband in the second container.

38. The inspection system of claim 32, wherein the reflecting means comprises a corner-reflecting cube.

39. The inspection system of claim 32, wherein the container comprises a spare tire mounted on an automobile comprising a sheet metal wall located behind the spare tire, and wherein the reflecting means comprises said sheet metal wall.

40. The inspection system of claim 32, wherein the transceiver means, reflecting means, processing means, and alerting means are packaged as a hand-held, portable unit;

wherein the portable unit comprises a frame with a pair of support posts;

wherein the transceiver means is mounted on one support post; and wherein the reflecting means is mounted on the other support post.

41. A method of inspecting a non-metallic container having unknown contents, comprising the steps of:

placing the container in-between transmitting means and receiving means;

generating and transmitting a test microwave signal towards the container;

receiving the test microwave signal after having passed through the container;

processing the received test signal, comprising detecting, analyzing and comparing at least one characteristic property of the received test microwave signal with the same characteristic property of a received baseline microwave signal generated by passing a baseline microwave signal through a substantially similar container having normal contents; and generating an alert indicating the presence of abnormal contents within the container, based on results of the comparison of the test signal with the baseline signal.

42. The method of claim 41, further comprising generating a continuous microwave signal.

43. The method of claim 42, further comprising sweeping the frequency of the microwave signal from a minimum value to a maximum value.

44. The method of claim 42, further comprising measuring the amplitude of the received microwave signal.

45. The method of claim 42, further comprising measuring the phase of the received microwave signal.

46. The method of claim 42, further comprising generating, transmitting, and receiving a plurality of microwave signals from a plurality of different sized transmitting and receiving means.

47. The method of claim 41, further comprising generating a short pulse of microwave radiation, having a duration between approximately 5 ps and 100 ns.

48. The method of claim 47, further comprising measuring a direct time-of-flight of a direct microwave pulse as it travels directly from the transmitting means to the receiving means, while passing through the container.

49. The method of claim 48, further comprising calculating the direct time delay between the measured direct time-of-flight of the direct microwave pulse, and the baseline direct time-of-flight (as determined on a container without contraband); comparing the calculated direct time delay with a threshold direct value; and indicating an alert if the calculated direct time delay exceeds the threshold direct value.

50. The method of claim 48, wherein measuring a direct time-of-flight of a direct microwave pulse as it travels directly from the transmitting means to the receiving means, while passing through the container, comprises:

using a pickoff to divert a small amount of energy from the short pulse of microwave radiation generated by an ultra-short microwave pulser to a trigger module;

using the trigger module to generate a trigger signal in response to receiving the small amount of energy diverted by the pickoff;

sending the trigger signal to a timer;

sending the signal received by the receiving means to the timer; and using the timer to detect the time at which the pulse is received by the receiving means, relative to the time when the pulse was launched by the microwave pulser, via the trigger signal.

51. The method of claim 47, further comprising measuring an echo time-of-flight of an echo microwave pulse as it travels from the transmitting means to the receiving means, and reflecting from at least two internal surfaces inside of the container, while passing through the container.

52. The method of claim 51, further comprising monitoring the receiver for a disappearance of the first echo pulse, thereby indicating contraband hidden within the container.

53. The method of claim 51, further comprising calculating the echo time delay between the measured echo time-of-flight of the echo microwave pulse, and the baseline echo time-of-flight (as determined on a container without contraband); comparing the calculated echo time delay with a threshold echo value; and indicating an alert if the calculated echo time delay exceeds the threshold echo value.

54. A method of inspecting a tire mounted on a vehicle, the tire possibly containing hidden contraband, comprising the steps of:

placing the tire in-between transmitting means and receiving means;

generating and transmitting a test microwave signal through the tire;

receiving the test microwave signal after passing through the tire;

processing the received test signal, comprising; analyzing and comparing at least one characteristic property of the received test microwave signal with the same characteristic property of a received baseline microwave signal generated by passing a baseline microwave signal through a substantially similar tire without contraband hidden inside; and generating an alert indicating the presence of contraband hidden within the tire, based on results of the comparison of the test signal with the baseline signal;

wherein the transmitting means and the receiving means are coaxially aligned and diametrically opposed to one another on opposite sides of the tire; and are positioned so that a microwave signal launched by the transmitting means passes through at least both sidewalls of the tire before being received by the receiving means.

55. The method of claim 54, further comprising rotating the tire during inspection while the vehicle is parked.

56. The method of claim 54, further comprising adjusting the vertical position of both the transmitting and receiving means, relative to the tire.

57. The method of claim 54, further comprising driving the vehicle through an inspection station comprising two parallel rows of transmitters and receivers, comprising a transmitting row having a plurality of transmitting means aimed to launch microwave signals in a direction perpendicular to the direction of the tire's travel while the vehicle is moving; and further comprising a receiving row having a plurality of receiving means aimed to receive the corresponding transmitted microwave signals; wherein the rows are sufficiently long to permit inspection of at least one complete revolution of the tire.

58. The method of claim 54, further comprising moving a movable transporter device into position around at least one tire, prior to inspecting the tire.

59. The method of claim 54, further comprising:

placing a second tire in-between the transmitting means and the receiving means, adjacent to the first tire; and transmitting the microwave signal through the two adjacent tires.

60. The method of claim 54, further comprising transmitting a total radiated power from the transmitting means that is less than or equal to 10 milliwatts; a level that poses no safety hazard to people.

61. A method of inspecting a non-metallic container having unknown contents, comprising, in the order presented:

a) placing the container in-between transceiving means and reflecting means, wherein the transceiving means and the reflecting means are coaxially aligned and diametrically opposed to one another on opposite sides of the container;

b) launching a test microwave signal in a forward direction towards the container;

c) passing the test signal through the container in the forward direction;

d) reflecting the test microwave signal from the reflecting means after having passed through the container in the forward direction;

e) passing the reflected test signal back through the container in a backward direction;

f) receiving the reflected test signal, after having passed back through the container in the backward direction;

g) processing the received reflected test signal, comprising; detecting, analyzing and comparing at least one characteristic property of the received reflected test microwave signal with the same characteristic property of a received reflected baseline microwave signal generated by performing steps a) through f) on a substantially similar container having normal contents; and h) generating an alert indicating the presence of abnormal contents within the container, based on results of the comparison of the received reflected test signal with the received reflected baseline signal.

62. The method of claim 41, further comprising combining information about attenuation and time delay characteristics of the received microwave signal to make a more reliable prediction of possible hidden contraband.

63. The method of claim 41, further comprising transmitting a total radiated power from the transmitting means that is less than or equal to 10 milliwatts; a level that poses no safety hazard to people.

64. The method of claim 41, further comprising generating the microwave signal at a frequency of 5.8 GHZ, which corresponds to a Special ISM (Instrument, Scientific, and Medical) fixed frequency that doesn't require special approval of an operating license.

65. The method of claim 41, further comprising generating the microwave signal at a frequency of about 10 GHZ, which allows an inspection system to be constructed using commercially available off-the-shelf components that are used in radar speed guns operating in the X-band at about 10 GHZ.

66. The inspection system of claim 61, wherein the reflecting means comprises a corner-reflecting cube.

67. The method of claim 61, wherein the container comprises a spare tire mounted on a vehicle having a sheet metal wall located behind the spare tire, and wherein the reflecting means comprises the sheet metal wall of the vehicle.

* * * * *